(12) United States Patent
Chen et al.

(10) Patent No.: US 8,425,931 B2
(45) Date of Patent: *Apr. 23, 2013

(54) BIODEGRADABLE HYALURONIC ACID DERIVATIVE

(75) Inventors: Jui-Hsiang Chen, Hsinchu (TW);
Bin-Hong Tsai, Kaohsiung (TW);
Hsuen-Tseng Chang, Kaohsiung (TW);
Muh-Lan Chen, Hsinchu (TW);
Yu-Hua Chen, Taichung (TW);
Shu-Hua Jan, Changhua (TW);
Mei-Jung Liu, Miaoli (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/548,719

(22) Filed: Jul. 13, 2012

(65) Prior Publication Data

US 2012/0283429 A1    Nov. 8, 2012

Related U.S. Application Data

(63) Continuation of application No. 12/860,051, filed on Aug. 20, 2010, now Pat. No. 8,313,765, which is a continuation-in-part of application No. 10/992,387, filed on Nov. 18, 2004, now Pat. No. 7,780,982.

(30) Foreign Application Priority Data

Dec. 4, 2003 (GB) .................................. 0328168.0

(51) Int. Cl.
*A61K 9/127* (2006.01)

(52) U.S. Cl.
USPC .......................................................... 424/450

(58) Field of Classification Search ........................ None
See application file for complete search history.

(56) References Cited

U.S. PATENT DOCUMENTS

| | | | |
|---|---|---|---|
| 4,851,521 A | 7/1989 | della Valle et al. | |
| 4,957,744 A | 9/1990 | della Valle et al. | |
| 5,122,598 A | 6/1992 | della Valle et al. | |
| 5,202,431 A | 4/1993 | della Valle et al. | |
| 5,336,767 A | 8/1994 | della Valle et al. | |
| 5,442,053 A | 8/1995 | della Valle et al. | |
| 5,462,976 A | 10/1995 | Matsuda et al. | |
| 5,510,418 A | 4/1996 | Rhee et al. | |
| 5,705,270 A | 1/1998 | Soon-Shiong et al. | |
| 5,856,299 A | 1/1999 | Righetto et al. | |
| 6,322,805 B1 | 11/2001 | Kim et al. | |
| 2005/0112172 A1 | 5/2005 | Pacetti | |

FOREIGN PATENT DOCUMENTS

| GB | 2 151 244 | 7/1985 |
|---|---|---|
| JP | 2001348401 | 12/2001 |
| SK | 46197 | 3/1990 |
| WO | WO 99/43728 | 9/1999 |
| WO | WO 02/098923 | 12/2002 |

*Primary Examiner* — Anand Desai
*Assistant Examiner* — Melissa Mercier
(74) *Attorney, Agent, or Firm* — McClure, Qualey & Rodack, LLP

(57) ABSTRACT

The description provides a biodegradable hyaluronic acid derivative including at least one modified hyaluronic acid repeating unit represented by the formula (HA)-[O(C=O)NH-M]p, wherein HA is a unit including N-acetyl-D-glucosamine and D-glucuronic acid, M is a modifying moiety containing a $C_{2-16}$ hydrocarbyl group, and p is an integer of 1 to 4.

6 Claims, 21 Drawing Sheets

FIG. 11 Mono-functional PLLA

HA-graft-PLLA

BIODEGRADABLE HYALURONIC ACID DERIVATIVE

CROSS REFERENCE TO RELATED APPLICATIONS

This application is a Continuation of pending U.S. patent application Ser. No. 12/860,051, filed Aug. 20, 2010 and entitled "Biodegradable Hyaluronic Acid Derivative, Biodegradable Polymeric Micelle Composition and Pharmaceutical or Bioactive Composition", which is a Continuation-In-Part of pending U.S. patent application Ser. No. 10/992,387, filed Nov. 18, 2004 and entitled "Biodegradable Hyaluronic Acid Derivative and Biodegradable Polymeric Micelle Composition" which claims priority to United Kingdom application number 0328168.0, filed Dec. 4, 2003, both of which are disclosed herein in their entirety.

TECHNICAL FIELD

The present description relates to a biodegradable hyaluronic acid derivative, and more particularly to a biodegradable hyaluronic acid derivative resulting from the reaction of hydroxy groups in hyaluronic acid and isocyanate groups in an isocyanate group-containing compound via a urethane linkage or degradable ester linkage.

BACKGROUND

Hyaluronan or hyaluronic acid is a linear mucopolysaccharide constituted by N-acetyl-D-glucosamine and D-glucuronic acid repeating units. Hyaluronic acid was first found in the vitreous body of a cattle eye by Meyer and Palmer in 1934, and then was found in other tissues such as extracellular matrix (ECM) and synovial fluid of the joints. Hyaluronic acid is a viscoelastic fluid filled in the space between cells and collagenous fibers and coated on some epidermal tissues. Hyaluronic acid plays an important role in the biological organism, firstly as a mechanical support of the cells of many tissues, such as the skin, the tendons, the muscles and cartilage. Hyaluronic acid also performs other functions in the biological processes, such as moistening of tissues, lubrication, and cellular migration.

Hyaluronic acid may be extracted from natural tissues, such as a rooster's comb, or also from certain bacteria. The molecular weight of hyaluronic acid obtained by extraction varies due to the source and the extraction process and is generally in the range of several millions to several tens of millions Dalton.

Hyaluronic acid, its molecular fractions and its salts have been used in pharmaceutical, surgical and cosmetic fields and in the field of biodegradable polymer materials. However, since hyaluronic acid is very expensive and is biodegraded quite easily, its application is limited. In past years, many methods have been developed to modify hyaluronic acid in order to increase its resistance to biodegradation.

In U.S. Pat. No. 5,462,976, tertiary amine salt of a glycosaminoglycan (such as hyaluronic acid) is reacted with a photoreactive compound to undergo esterification. The ester product is then exposed to UV radiation to form a crosslinked water-insoluble glycosaminoglycan derivative.

Francesco della Valle et al. at Fidia, S.p.A. in U.S. Pat. No. 4,851,521 discloses a process for preparing esters of hyaluronic acid. Hyaluronic acid is converted into an ammonium salt that can be dissolved in an organic solvent, and is then reacted with an aliphatic type alcohol to form an ester bond on hyaluronic acid. An ester linkage is formed by the reaction of the carboxyl group (COOH) on hyaluronic acid and the hydroxy group on the alcohol.

Francesco della Valle et al. in U.S. Pat. No. 4,957,744 discloses a process for preparing cross-linked esters on hyaluronic acid. Hyaluronic acid is first converted into an ammonium salt. Then, a polyhydric alcohol is used to react with more than two carboxyl groups (COOH) on hyaluronic acid, thus forming a cross-linked esterified hyaluronic acid.

Francesco della Valle et al. in U.S. Pat. No. 5,122,598 discloses a process for preparing polysaccharide esters. Polysaccharide, such as carboxymethylcellulose and carboxymethylchitin, is first converted into an ammonium salt. Then, an alcohol is used to react with the carboxyl group (COOH) on hyaluronic acid, thus forming a polysaccharide ester.

Francesco della Valle et al. in U.S. Pat. No. 5,202,431 discloses a process for preparing partial esters of hyaluronic acid. Hyaluronic acid is first converted into an ammonium salt. Then, an aliphatic alcohol is used to react with the carboxyl group (COOH) on hyaluronic acid. Then, the hyaluronic acid ester is salified with a therapeutically active amine.

Francesco della Valle et al. in U.S. Pat. No. 5,336,767 discloses a process for preparing total or partial esters of hyaluronic acid. Hyaluronic acid is first converted into an ammonium salt. Then, a pharmacologically active alcohol, such as cortisone, hydrocortisone or prednisone is reacted with the carboxyl group (COOH) on hyaluronic acid via an ester linkage.

Francesco della Valle et al. in U.S. Pat. No. 5,442,053 discloses a composition including hyaluronic acid and a pharmacologically active substance. A hyaluronic acid fraction with a molecular weight between 50,000 and 100,000 is particularly suitable for wound healing and hyaluronic acid with a molecular weight between 500,000 and 730,000 is particularly suitable for intraarticular injection.

Zefferino Righetto et al. in U.S. Pat. No. 5,856,299 discloses highly reactive esters of carboxy polysaccharide and carboxy polysaccharides derived therefrom. Hyaluronic acid is first converted into a salt of hyaluronic acid capable of being dissolved in an organic solvent. Then, an aromatic alcohol is used to react with the carboxyl group (COOH) on hyaluronic acid, thus forming a highly reactive esterified hyaluronic acid suitable for biomedical and pharmaceutical fields.

However, there is still a need to modify hyaluronic acid in order to improve its properties or various applications.

BRIEF SUMMARY

The description provides a biodegradable hyaluronic acid derivative comprising at least one modified hyaluronic acid repeating unit represented by the formula (HA)-[O(C=O)NH-M]p, wherein HA is a unit including N-acetyl-D-glucosamine and D-glucuronic acid, M is a modifying moiety containing a $C_{2-16}$ hydrocarbyl group, and p is an integer of 1 to 4.

The description also provides a biodegradable hyaluronic acid derivative comprising at least one modified hyaluronic acid repeating unit represented by the formula (HA)-[O(C=O)NH-M]p, wherein HA is a unit including N-acetyl-D-glucosamine and D-glucuronic acid, M is a modifying moiety containing a prepolymer, and p is an integer of 1 to 4, and wherein the prepolymer is hydrophilic or amphiphilic, or is a combination of hydrophilic, amphiphilic and hydrophobic prepolymers.

The description further provides a biodegradable polymeric micelle composition comprising a hydrophilic medium and a biodegradable hyaluronic acid derivative comprising a modified hyaluronic acid repeating unit represented by the formula (HA)-[O(C=O)NH-M]p, wherein HA is a unit including N-acetyl-D-glucosamine and D-glucuronic acid, M is a modifying moiety containing a $C_{2-16}$ hydrocarbyl group or a prepolymer, and p is an integer of 1 to 4, wherein the prepolymer is amphiphilic, or is a combination of hydrophilic, amphiphilic and hydrophobic prepolymers, and wherein the biodegradable hyaluronic acid derivative forms micelles.

The description further provides a pharmaceutical or bioactive composition comprising a hydrophilic medium and a biodegradable hyaluronic acid derivative comprising a modified hyaluronic acid repeating unit represented by the formula (HA)-[O(C=O)NH-M]p, wherein HA is a unit including N-acetyl-D-glucosamine and D-glucuronic acid, M is a modifying moiety containing a $C_{2-16}$ hydrocarbyl group or a prepolymer, and p is an integer of 1 to 4, wherein the prepolymer is a hydrophilic or amphiphilic prepolymer, or is a combination of hydrophilic, amphiphilic and hydrophobic prepolymers; and a pharmaceutically active molecule or a bioactive molecule entrapped within a nano particle formed by the biodegradable hyaluronic acid derivative or adsorbed by the biodegradable hyaluronic acid derivative.

A detailed description is given in the following embodiments with reference to the accompanying drawings.

BRIEF DESCRIPTION OF THE DRAWINGS

The present description can be more fully understood by reading the subsequent detailed description and examples with references made to the accompanying drawings, wherein.

DETAILED DESCRIPTION

The following description is of the best-contemplated mode of carrying out the description. This description is made for the purpose of illustrating the general principles of the description and should not be taken in a limiting sense. The scope of the description is best determined by reference to the appended claims.

Figure 1A:
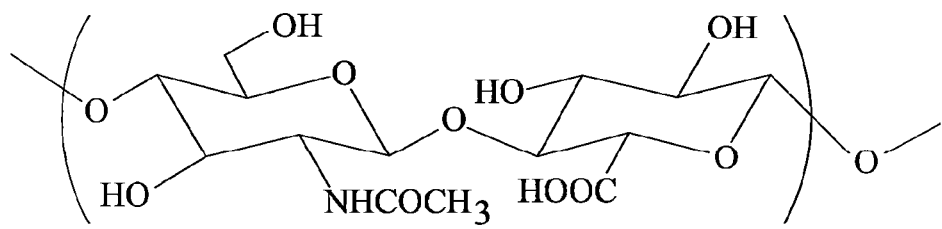
FIG. 1a shows a native hyaluronic acid repeating unit, which is not modified.

The native hyaluronic acid is a linear mucopolysaccharide constituted by N-acetyl-D-glucosamine and D-glucuronic acid repeating units, as shown in FIG. 1a.

The present description introduces a modifying moiety to the hydroxy group (—OH) on the native hyaluronic acid via a urethane linkage [—O(C=O)NH—]. The modifying moiety can contain a $C_{2-16}$ hydrocarbyl group or a prepolymer.

In other words, the modified hyaluronic acid (hyaluronic acid derivative) of the present description includes a modified hyaluronic acid repeating unit represented by the formula

(HA)-[O(C=O)NH-M]p          (1)

wherein HA is a unit including N-acetyl-D-glucosamine and D-glucuronic acid, M is a modifying moiety containing a $C_{2-16}$ hydrocarbyl group or a prepolymer, and p is 1 to 4.

Figure 1B:
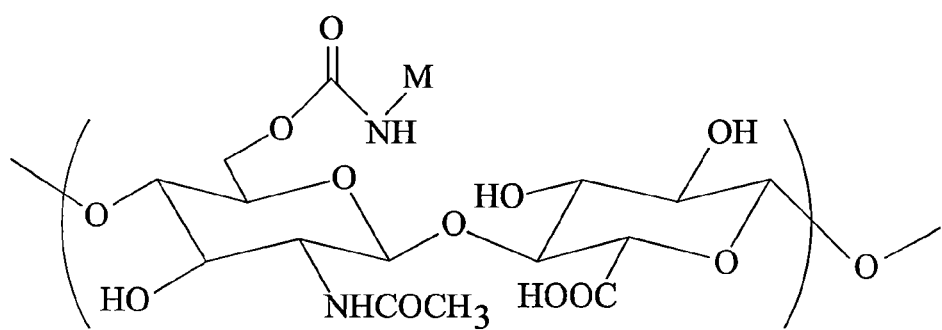
FIG. 1b shows a modified hyaluronic acid repeating unit bearing one modifying moiety (M) via a urethane linkage.

FIG. 1b illustrates the chemical structure of formula (1), in which p is 1.

On the hyaluronic acid derivative of the present description, the —COOH groups and the —NHCOCH$_3$ groups can remain intact, or, some of the —COOH groups and/or some of the —NHCOCH$_3$ groups can be substituted according to practical requirements. For example, the —COOH group can be converted into a —COOM$_1$ group, wherein M$_1$ can be an alkaline metal, an alkaline earth metal, ammonium, or aluminum. Thus, the salt of the hyaluronic acid derivative of the present description is within the scope of the present description.

In addition, according to the present description, the —OH groups in the native hyaluronic acid can be totally or partially modified. Totally modification means that all of the —OH groups on the native hyaluronic acid are modified via a urethane or degradable ester linkage as described above (p=4).

Figure 1C:
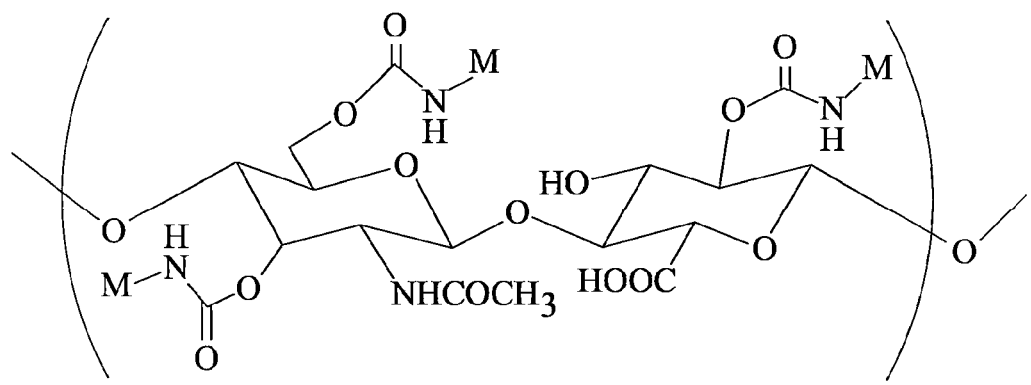
FIG. 1c shows a modified hyaluronic acid repeating unit bearing three modifying moieties (M) via a urethane linkage.

Partially modification means that some of the —OH groups on the native hyaluronic acid are modified, but some are not modified. That is to say, the hyaluronic acid derivative of the present description can include a plurality of native hyaluronic acid repeating units (p=0, as shown in FIG. 1a) and a plurality of modified hyaluronic acid repeating units. The modified hyaluronic acid repeating units may have different modification extents. That is, the modified hyaluronic acid repeating units with p=1, 2, 3, and 4 may be present in the hyaluronic acid derivative. FIG. 1b shows a modified hyaluronic acid repeating unit bearing one modifying moiety (M) via a urethane linkage (p=1). FIG. 1c shows a modified hyaluronic acid repeating unit bearing three modifying moieties (M) via a urethane linkage (p=3).

In addition, all of the hyaluronic acid repeating units can be modified (that is, no native hyaluronic acid repeating unit remains), but not all of the —OH groups in the native hyaluronic acid are modified. For example, the hyaluronic acid derivative of the present description can include a first modified hyaluronic acid repeating unit (FIG. 1b, p=1), a second modified hyaluronic acid repeating unit (p=2), a third modified hyaluronic acid repeating unit (FIG. 1c, p=3), a fourth modified hyaluronic acid repeating unit (p=4), or a mixture thereof, but no native hyaluronic acid repeating unit (p=0) is present.

For better understanding, the biodegradable hyaluronic acid derivative of the present description can be classified into two categories:

(A) a biodegradable hyaluronic acid derivative substituted with a short chain moiety (when M is a modifying moiety containing a $C_{2-16}$ hydrocarbyl group), and (B) a biodegradable hyaluronic acid copolymer grafted with a prepolymer (when M is a modifying moiety containing a prepolymer).

Category (A): Hyaluronic acid derivative substituted with a short chain moiety

The hyaluronic acid derivative in category (A) of the present description includes a modified hyaluronic acid repeating unit represented by the formula

Wherein HA is a unit including N-acetyl-D-glucosamine and D-glucuronic acid, M is a modifying moiety containing a $C_{2-16}$ hydrocarbyl group, and p is an integer of 1 to 4.

Figure 1D:
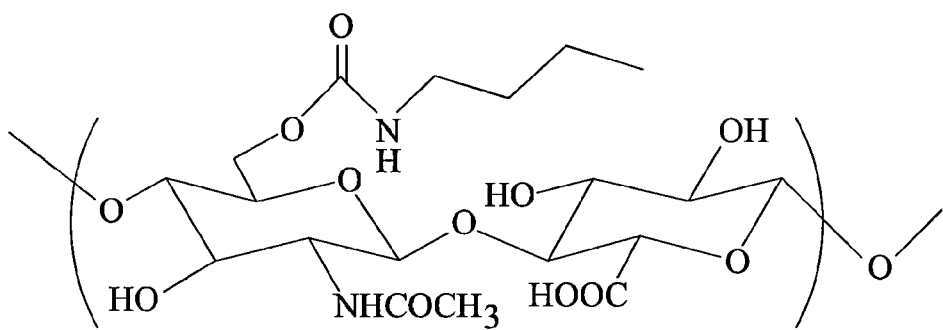
FIG. 1d shows a modified hyaluronic acid repeating unit bearing butyl groups via a urethane linkage.

FIG. 1d illustrates one example of formula (1) in category (A) of the present description, in which M is butyl and p is 1.

Preferably, M can be a $C_{2-16}$ alkyl group, more preferably a $C_{4-12}$ alkyl group.

The process for preparing the biodegradable hyaluronic acid derivative in category (A) of the present description is described below. A hydroxy group (—OH) on hyaluronic acid is reacted with a $C_{2-16}$ hydrocarbyl isocyanate. (The $C_{2-16}$ hydrocarbyl isocyanate can be formed from the reaction of a $C_{2-16}$ alcohol with an isocyante group-containing compound.) Thus, the $C_{2-16}$ hydrocarbyl (short chain moiety) is introduced onto the hydroxy group via a urethane [—O(C=O)—NH—] linkage or degradable ester[-O(C=O)—] linkage, forming the biodegradable hyaluronic acid derivative in category (A).

The hyaluronic acid starting material does not need to be a native hyaluronic acid, but can be a hyaluronic acid derivative. That is to say, the starting material can be a hyaluronic acid where the —COOH group or the —NHCOCH$_3$ group is substituted. Also, even the hydroxy group (—OH) in the hyaluronic acid starting material can be partially substituted, as long as there are still residual —OH groups for introducing the short chain moiety via the urethane linkage.

For example, in order to allow the reaction to be performed in an organic solvent, the hyaluronic acid starting material can be a hyaluronic acid salt capable of being dissolved in an organic solvent. For example, the hyaluronic acid having a hydroxy group (starting material) can be a quaternary ammonium salt of hyaluronic acid. That is, the —COOH group in the native hyaluronic acid is converted into a COON (CH$_2$CH$_2$CH$_2$CH$_3$)$_4$ group, since the modification of hyaluronic acid complete, the COON(CH$_2$CH$_2$CH$_2$CH$_3$)$_4$ group is reduced as a —COONa group or —COOH group by a saline solution or ion exchange resin.

The hyaluronic acid having a hydroxy group (starting material) can have a molecular weight of 2,000 to 3500,000.

Preferably, the $C_{2-16}$ hydrocarbyl isocyanate (modifying compound) can be a $C_{2-16}$ alkyl isocyanate, and more preferably a $C_{4-12}$ alkyl isocyanate. Representative examples include butyl isocyanate, sec-butyl isocyanate, octyl isocyanate, and dodecyl isocyanate.

The reaction can be conducted at a temperature of 10° C. to 90° C. in the presence of a catalyst such as di-n-butyltin dilaurate, di-n-butyltin diacetate, sodium phenate, ferric chloride, copper acetylacetonate, zinc naphthenate, tributylphosphine, 1,4-diazabicyclo[2,2,2]octane(DABCO), an organosilver complex, or the combination thereof.

Category (B): Hyaluronic acid derivative grafted with prepolymer

The hyaluronic acid derivative in category (B) of the present description includes a modified hyaluronic acid repeating unit represented by the formula

Wherein HA is a unit including N-acetyl-D-glucosamine and D-glucuronic acid, M is a modifying moiety containing a prepolymer, and p is an integer of 1 to 4.

Figure 1E:
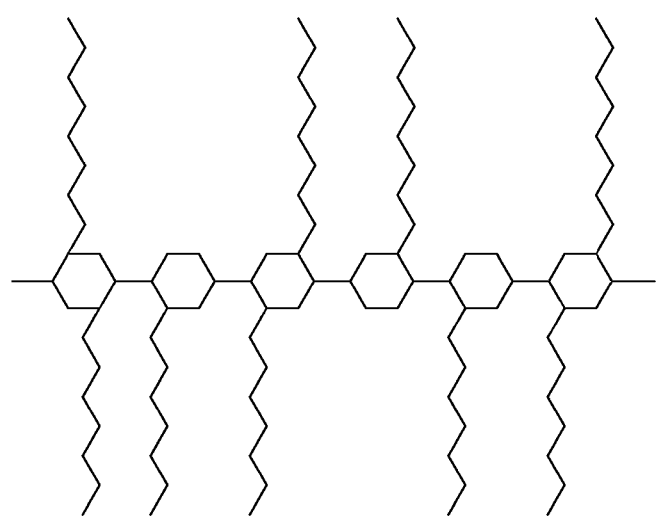
FIG. 1e is a chemical structure of the comb-like shaped hyaluronic acid graft copolymer.

When M is a modifying moiety containing a prepolymer, the hyaluronic acid derivative including a plurality of the formula (1) repeating units can constitute a comb-like, or a brush-like shaped graft copolymer as shown in FIG. 1e.

According to the present description, the prepolymer grafted with hydroxy group on hyaluronic acid can be hydrophobic, hydrophilic or amphiphilic, or can be a combination of a hydrophobic, hydrophilic and amphiphilic prepolymers. Preferably, the prepolymer suitable for use is a biodegradable molecule, or is a hydrophilic or amphiphilic prepolymer with biocompatibility. The prepolymer can be the same or different. For example, the biodegradable hydrophobic prepolymer can be a biodegradable polyester-containing prepolymer. The suitable biodegradable polyester-containing hydrophobic prepolymer may include polycaprolactone (PCL), poly L-lactide (PLLA), polylactic acid (PLA), polyglycolic acid (PGA), poly-lactic-co-glycolic acid copolymer (PLGA copolymer), polycaprolactone-polylactic acid copolymer (PCL-PLA copolymer) or the combination thereof.

The biocompatible hydrophilic prepolymer may include polyvinylpyrridone, polyethylene glycol, polyethylene oxide, polyvinylalcohol, or the combination thereof. The biocompatible amphiphilic prepolymer may include polycaprolactone-polyethylene glycol copolymer (PCL-PEG copolymer), polylactic acid-polyethylene glycol copolymer (PLA-PEG copolymer), polyglycolic acid-polyethylene glycol copolymer (PGA-PEG copolymer), or the combination thereof, and the content of hydrophobic region in the biocompatible amphiphilic prepolymer is about 1%-99%, or preferably about 1%-80%.

The process for preparing the biodegradable hyaluronic acid derivative in category (B) of the present description is described below. A prepolymer bearing a hydroxy group is reacted with a diisocyanate compound to form a modifying compound having an isocyanate (—N=C=O) group via a urethane [—O(C=O)—NH—] linkage. Finally, a hydroxy group (—OH) on hyaluronic acid is reacted with the modifying compound having an isocyanate (—N=C=O) group to form the biodegradable hyaluronic acid derivative in category (B) via a urethane [—O(C=O)—NH—] linkage. Alternatively the polymer is directly bound to the biodegradable hyaluronic acid derivative in category (B) through a degradable ester group.

The prepolymer grafted onto the —OH position of hyaluronic acid can be the same or different. Different prepolymers can be mixed and then grafted onto the hyaluronic acid at the same time. Or, different prepolymers can be grafted onto the hyaluronic acid sequentially and separately.

The diisocyanate suitable for use in the present description can be an aliphatic type isocyanate, such as hexamethylene diisocyanate or 4,4'-methylenebis(cyclohexyl isocyanate), or can be an aromatic type isocyanate, such as 4,4'-diphenylmethane diisocyanate or 1,4 phenylene diisocyanate.

The hyaluronic acid starting material does not need to be a native hyaluronic acid, but can be a hyaluronic acid derivative. That is to say, the starting material can be a hyaluronic acid where the —COOH group or the —NHCOCH$_3$ group is substituted. Also, even the hydroxy group (—OH) on the hyaluronic acid starting material can be partially substituted, as long as there are still residual —OH groups for introducing the short chain moiety via the urethane linkage or degradable ester linkage.

For example, in order to perform the reaction in an organic solvent, the hyaluronic acid starting material can be a hyaluronic acid salt capable of being dissolved in an organic solvent. For example, the hyaluronic acid having a hydroxy group (starting material) can be a quaternary ammonium salt of hyaluronic acid. That is, the —COOH group in the native hyaluronic acid is converted into a —COON(Bu)$_4$ group.

The hyaluronic acid having a hydroxy group (starting material) can have a molecular weight of 2,000 to 3500,000.

The prepolymer suitable for use in the present description can be a biodegradable or biocompatible prepolymer, and can be a hydrophobic, hydrophilic or amphiphilic prepolymer or the combination thereof. The biodegradable or biocompatible prepolymer bearing a hydroxy group or a functional group which is capable of forming a linkage with the OH group on the hyaluronic acid can have a molecular weight of 200 to 200000, or preferably 200 to 50000.

The suitable biodegradable hydrophobic prepolymers bearing a hydroxy group or a functional group which is capable of forming a linkage with the OH group on the hyaluronic acid may include polycaprolactone (PCL), poly L-lactide (PLLA), polylactic acid (PLA), polyglycolic acid (PGA), poly-lactic-co-glycolic acid copolymer (PLGA copolymer), polycaprolactone-polylactic acid copolymer (PCL-PLA copolymer), or the combination thereof The biocompatible hydrophilic prepolymers bearing a hydroxy group or a functional group which is capable of forming a linkage with the OH group on the hyaluronic acid may include polyvinylpyrridone, polyethylene glycol, polyethylene oxide, polyvinylalcohol, or the combination thereof The biodegradable or biocompatible amphiphilic prepolymers bearing a hydroxy group or a functional group which is capable of forming a linkage with the OH group on the hyaluronic acid may include polycaprolactone-polyethylene glycol copolymer (PCL-PEG copolymer), polylactic acid-polyethylene glycol copolymer (PLA-PEG copolymer), polyglycolic acid-polyethylene glycol copolymer (PGA-PEG copolymer), or the combination thereof.

The reaction can be conducted at a temperature of 10° C. to 90° C. in the presence of a catalyst such as di-n-butyltin dilaurate, di-n-butyltin diacetate, sodium phenate, ferric chloride, copper acetylacetonate, zinc naphthenate, tributylphosphine, 1,4-diazabicyclo[2,2,2]octane(DABCO), an organosilver complex, or the combination thereof.

Biodegradable Polymeric Micelle Composition

The hyaluronic acid derivative, either substituted with a short chain moiety (C$_{2-16}$ hydrocarbyl) as described above in category (A) or grafted with a biodegradable hydrophobic or amphiphilic prepolymer, or a combination of hydrophilic, amphiphilic and hydrophobic prepolymers as described above in category (B), can be dissolved in a hydrophilic medium. Thus, the hyaluronic acid derivative forms micelles.

Figure 2:
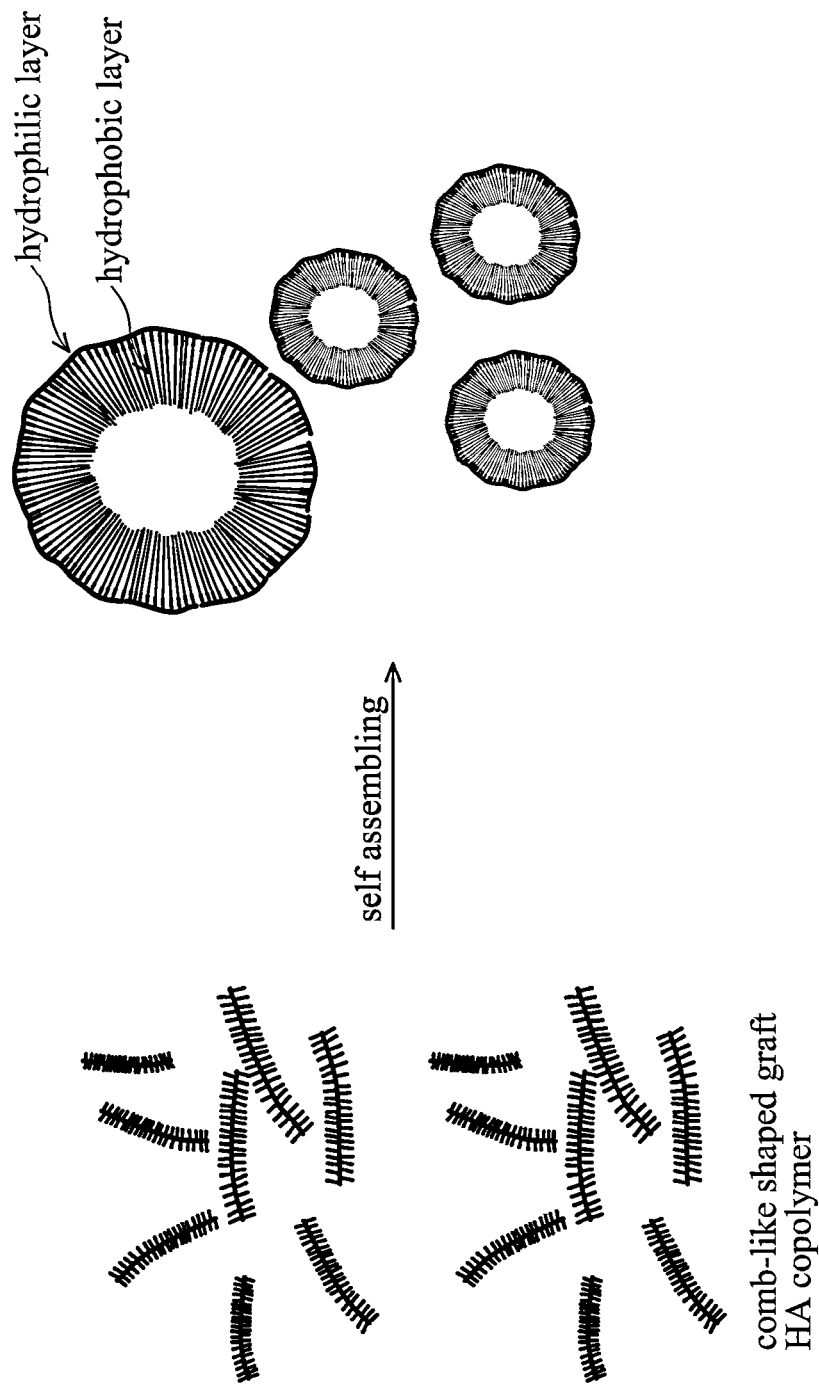
FIG. 2 illustrates the micelle structure of the hyaluronic acid derivative grafted with prepolymer.

For instance, when the biodegradable hyaluronic acid derivative is a comb-like shaped graft copolymer as described above and dissolved in a hydrophilic medium at a concentration higher than a critical micelle concentration, the comb-like shaped graft copolymer is self assembled into micelles. FIG. 2 shows the schematic diagram of the micelles. The hyaluronic acid main chains form an outer hydrophilic layer and the biodegradable hydrophobic prepolymers form an inner hydrophobic layer. A hydrophobic core is formed inside the hydrophobic layer.

In the micelle composition, the hyaluronic acid derivative can have a low critical micelle concentration in the range of 0.001 weight % to 5.0 weight %, or preferably 0.005 to 1.0 weight %, or most preferably 0.005 to 0.3 weight %. The hyaluronic acid derivative micelles can have a size of 10 nm to 500 nm, or preferably of 50 nm to 400 nm, or most preferably 50 to 300 nm.

The hydrophilic medium can be water or an aqueous solution.

Pharmaceutical or Bioactive Composition

A pharmaceutical or bioactive composition of the description may comprise a hydrophilic medium, a biodegradable hyaluronic acid derivative substituted with a short chain moiety (C$_{2-16}$ hydrocarbyl) as described above in category (A) or grafted with a prepolymer as described above in category (B), and a pharmaceutically active molecule or a bioactive molecule, wherein the prepolymer is a hydrophilic or amphiphilic prepolymer, or is a combination of hydrophilic, amphiphilic and hydrophobic prepolymers.

In one embodiment, the biodegradable hyaluronic acid derivative substituted with a short chain moiety (C$_{2-16}$ hydrocarbyl) or with a prepolymer as described above in category (B) grafted in the hydrophilic medium is able to form a nano particle to entrap the pharmaceutically active molecule or the bioactive molecule. In another embodiment, when the prepolymer grafted to a biodegradable hyaluronic acid derivative is an amphiphilic prepolymer or a combination of hydrophilic, amphiphilic and hydrophobic prepolymers, the pharmaceutically active molecule or the bioactive molecule will be entrapped within a nano particle formed by the biodegradable hyaluronic acid derivative in the hydrophilic medium. In further another embodiment, when the prepolymer grafted to a biodegradable hyaluronic acid derivative is a hydrophilic prepolymer, the pharmaceutically active molecule or the bioactive molecule in aqueous solution have a positive charge will be adsorbed by the biodegradable hyaluronic acid derivative in the hydrophilic medium.

Thus, the present description provides a pharmaceutical or bioactive composition including a hydrophilic medium, a biodegradable hyaluronic acid derivative comprising a modified hyaluronic acid, and a pharmaceutically active molecule or a bioactive molecule a pharmaceutically active molecule or a bioactive molecule entrapped within a nano particle formed by the biodegradable hyaluronic acid derivative or adsorbed by the biodegradable hyaluronic acid derivative.

The hyaluronic acid repeat unit represented by the formula

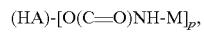

(HA)-[O(C=O)NH-M]$_p$, wherein HA is a unit including N-acetyl-D-glucosamine and D-glucuronic acid, M is a modifying moiety containing a $C_{2-16}$ hydrocarbyl group or a biodegradable hydrophobic prepolymer, and p is an integer of 1 to 4.

Preferably, the biodegradable hyaluronic acid derivative is a comb-like shaped graft copolymer and the pharmaceutically active or bioactive molecule is hydrophobic, such as anti-tumor drugs, anti-rejective drugs, or opioid analgesics.

Furthermore, a negative charge (—COO$^-$) resulting from the —COOH group of the hyaluronic acid derivative in category (A) or category (B) which is soluble in an aqueous solution. A pharmaceutically active or bioactive molecule with a positive charge causes a charge adsorption effect which makes the hyaluronic acid derivative in category (A) or category (B) to be a drug carrier. In other words, the pharmaceutically active or bioactive molecule is made to adsorb the hyaluronic acid derivative in category (A) or category (B).

The following examples are intended to illustrate the process and the advantages of the present description more fully without limiting its scope, since numerous modifications and variations will be apparent to those skilled in the art.

EXAMPLE

Series A Examples

Hyaluronic acid substituted with a short chain alkyl

Preparative Example 1

Preparation of Quaternary Ammonium Salt of Hyaluronic Acid 0.5 g sodium salt of hyaluronic acid was dissolved in 400 ml deionized water and stirred thoroughly. The solution was then eluted through a 25 cm Dowex 50×8 column in H$^+$ form for ion exchange. The resulting solution was neutralized with 40% tetrabutylammonium hydroxide solution and then freeze-dried. Yield: 0.667 g.

Example A-1

100% Substituted Butyl Urethane Derivative of Hyaluronic Acid (C4-HA)

Figure 3:
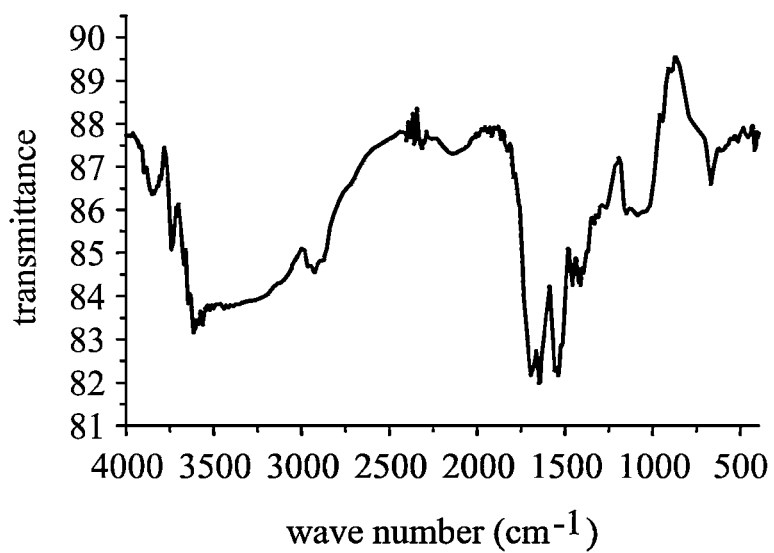
FIG. 3 is the IR spectrum of 100% substituted butyl urethane derivative of hyaluronic acid (C4-HA) prepared from Example A-1.

0.30 g (3×10$^{-3}$ meq, stoichiometrically 100% substituted) quaternary ammonium salt of hyaluronic acid prepared from Preparative Example 1 was dissolved in 60 ml DMSO (dimethylsulfoxide). 0.3 g butyl isocyanate (3×10$^{-3}$ meq) and 100 µl di-n-butyltin dilaurate (catalyst) were added in sequence. The reaction was kept at 65° C. for 8 hours and then quenched with DBA (di-butyl amine) The reaction mixture was dialyzed in a saturated sodium chloride aqueous solution with a dialysis membrane (MWCO=12,000-14,000), purified, exchanged from quaternary ammonium salt to sodium salt, and then freeze-dried to obtain C4-HA powder. The IR spectrum is shown in FIG. 3 and the urethane bond at 1710 cm$^{-1}$ can be seen.

Figure 8:
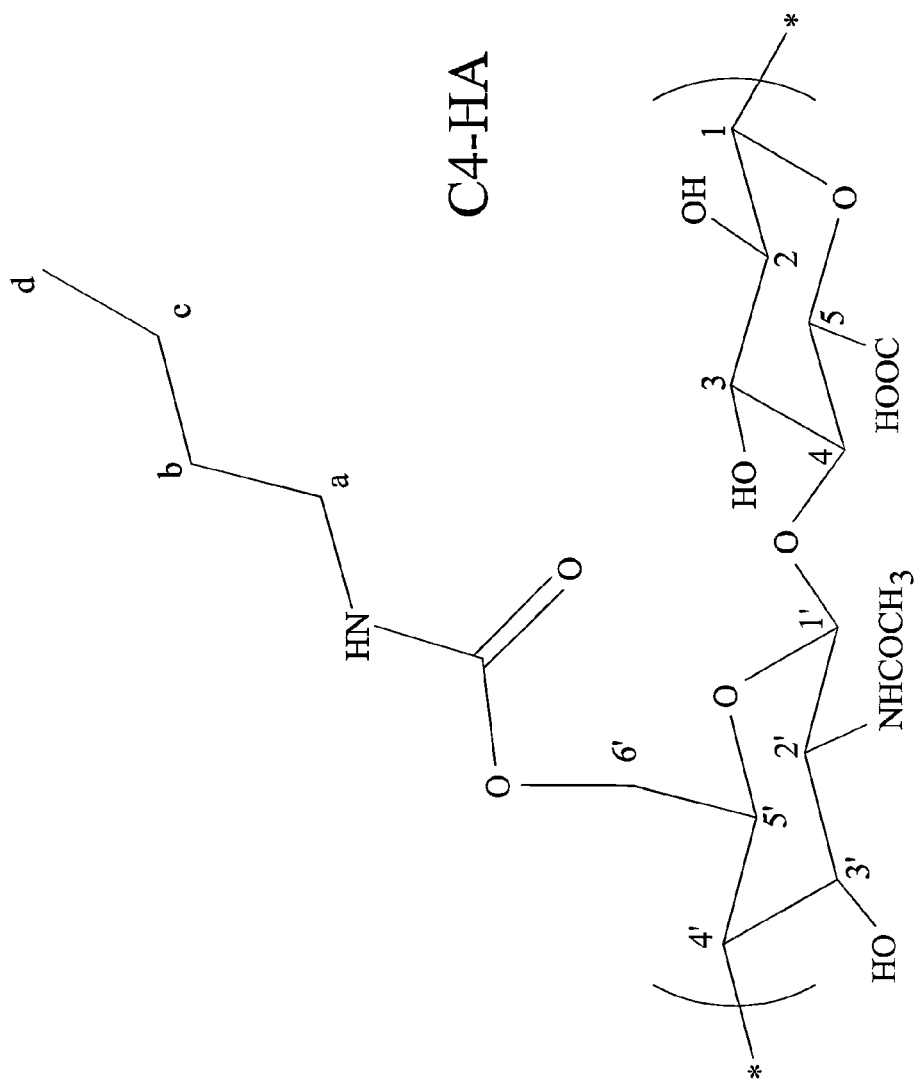
FIG. 8 shows the chemical structure of C4-HA, in which the protons on butyl group are labeled by a, b, c, and d, respectively.

FIG. 8 shows the chemical structure of C4-HA, in which the protons on butyl group are labeled by a, b, c, and d.

$^1$H NMR of C4-HA:

4.36-2.98 (m, hyaluronic acid backbone), 1.49~1.53 (m, H-a), 1.32~1.35 (m, H-b), 1.18~1.26 (m, H-c), 0.74~0.83 (m, H-d).

Figure 4A:
FIGS. 4a and 4b are SEM photographs of the freeze-dried C4-HA prepared from Example A-1.
Figure 4B:
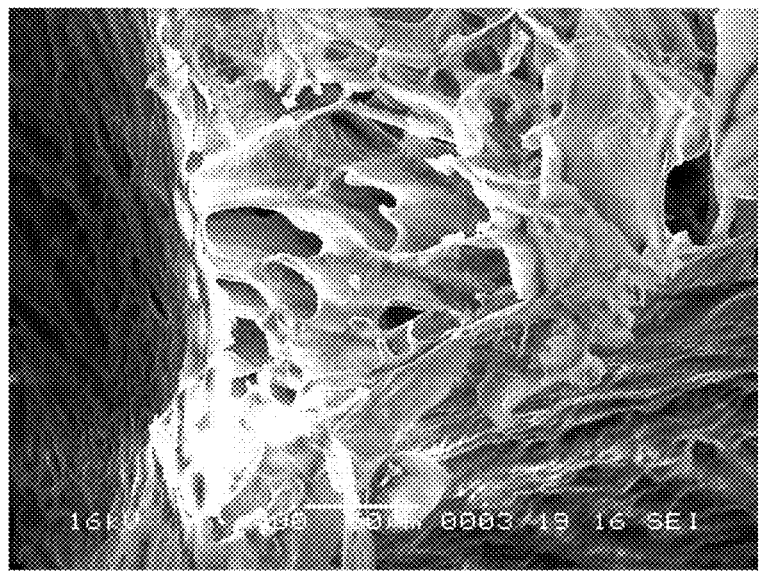

FIGS. 4a and 4b are SEM photographs of the freeze-dried C4-HA (100% substituted butyl urethane derivative of hyaluronic acid). It shows that the hyaluronic acid derivative is porous and suitable for serving as a "scaffold for cell or tissue" (bioresorbable porous matrix).

Figure 5:
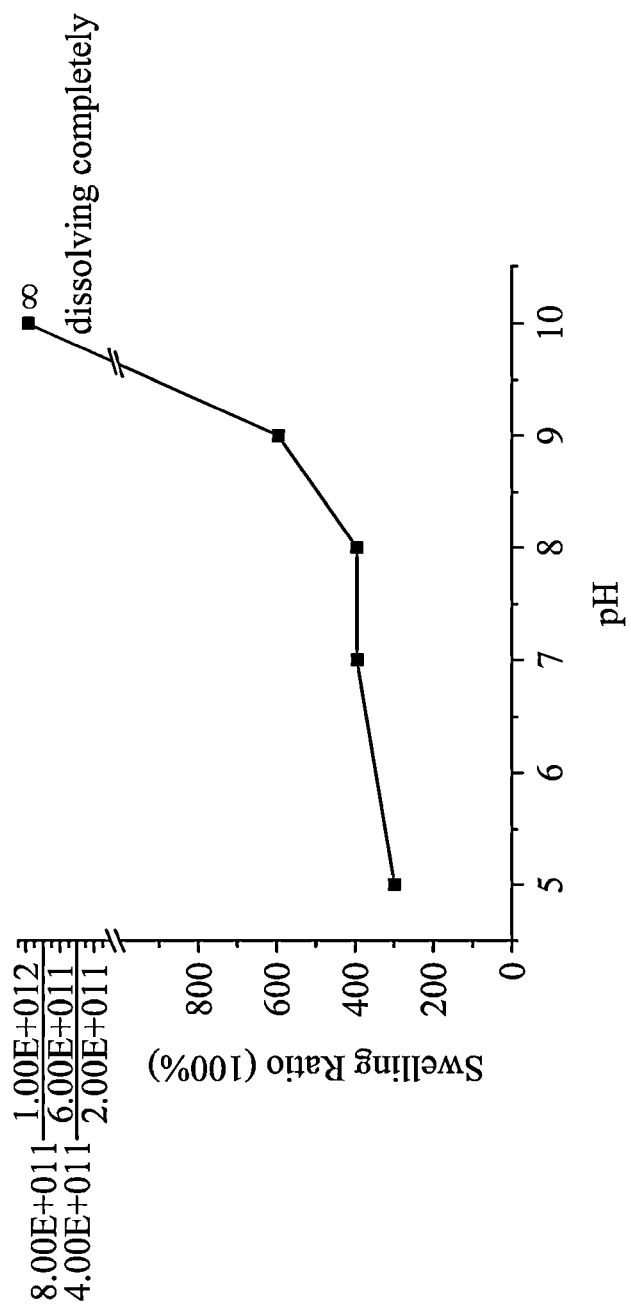
FIG. 5 shows the relationship between the swelling ratio and the pH of C4-HA prepared from Example A-1.

FIG. 5 shows the relationship between the swelling ratio and the pH of C4-HA.

Cytotoxicity Test:

C4-HA was assessed for cytotoxicity using L929 cell line according to the ASTM F895 method. Cell line L929 was cultured in a 6-well culture plate. After 24 hours, a confluent monolayer was formed. Culture supernatant was removed from the plate and then 2 ml of agar medium was spread on the cells for solidification. The C4-HA powder was spread on a circle zone (diameter=1 cm) in the middle of the culture plate, incubated in a $CO_2$ incubator at 37° C. for 1 day, and then assessed for cytotoxicity by the neutral red dye method. The response index=zone index/lysis index. Zone index=0 indicates that there is no detected zone adjacent to or in the specimen. The result shows that the C4-HA material had no cytotoxicity response.

Example A-2

100% Substituted Sec-Butyl Urethane-Linked Hyaluronic Acid Derivative 0.30 g (3×10$^{-3}$ meq, stoichiometrically 100% substituted) quaternary ammonium salt of hyaluronic acid prepared from Preparative Example 1 was dissolved in 60 ml DMSO. 0.3 g sec-butyl isocyanate (3×10$^{-3}$ meq) and 100 µl di-n-butyltin dilaurate (catalyst) were added in sequence. The reaction was kept at 65° C. for 8 hours and then quenched with DBA (di-butyl amine) The reaction mixture was dialyzed in a saturated sodium chloride aqueous solution with a dialysis membrane (MWCO=12,000-14,000), purified, exchanged from quaternary ammonium salt to sodium salt, and then freeze-dried.

Example A-3

100% Substituted Octyl Urethane-Linked Hyaluronic Acid Derivative 0.37 g (3.7×10$^{-3}$ meq) quaternary ammonium salt of hyaluronic acid prepared from Preparative Example 1 was dissolved in 60 ml DMSO. 0.58 g octyl isocyanate (3.7×10$^{-3}$ meq) and 100 µl di-n-butyltin dilaurate (catalyst) were added in sequence. The reaction was kept at 65° C. for 8 hours and then quenched with DBA. The reaction mixture was dialyzed in a saturated sodium chloride aqueous solution with a dialysis membrane (MWCO=12,000-14,000), purified, exchanged from quaternary ammonium salt to sodium salt, and then freeze-dried.

Example A-4

50% Substituted Octyl Urethane-Linked Hyaluronic Acid Derivative 0.37 g (3.7×10$^{-3}$ meq) quaternary ammonium salt of hyaluronic acid prepared from Preparative Example 1 was dissolved in 60 ml DMSO. 0.29 g octyl isocyanate (1.85×10$^{-3}$ meq) and 100 µl di-n-butyltin dilaurate (catalyst) were added in sequence. The reaction was kept at 65° C. for 8 hours and then quenched with DBA. The reaction mixture was dialyzed in a saturated sodium chloride aqueous solution with a dialysis membrane (MWCO=12,000-14,000), purified, exchanged from quaternary ammonium salt to sodium salt, and then freeze-dried.

Example A-5

7% Substituted Octyl Urethane-Linked Hyaluronic Acid Derivative 2.0 g quaternary ammonium salt of hyaluronic acid (molecular weight=1040K) was dissolved in 180 ml DMSO. 0.3 g octyl isocyanate and 5.5 µl Stannous Octoate and 1.38 mg 1,4-diazabicyclo[2,2,2]octane (catalyst) were added in sequence. The reaction was kept at 65° C. for 16 hours and then quenched with DBA. The reaction mixture was dialyzed in a saturated sodium chloride aqueous solution with a dialysis membrane (MWCO=12,000-14,000), purified, exchanged from quaternary ammonium salt to sodium salt, and then freeze-dried.

Example A-6

10% Substituted Octyl Urethane-Linked Hyaluronic Acid Derivative 0.37 g ($3.7 \times 10^{-3}$ meq) quaternary ammonium salt of hyaluronic acid prepared from Preparative Example 1 was dissolved in 60 ml DMSO. 0.058 g octyl isocyanate ($3.7 \times 10^{-4}$ meq) and 100 µl di-n-butyltin dilaurate (catalyst) were added in sequence. The reaction was kept at 65° C. for 8 hours and then quenched with DBA. The reaction mixture was dialyzed in a saturated sodium chloride aqueous solution with a dialysis membrane (MWCO=12,000-14,000), purified, exchanged from quaternary ammonium salt to sodium salt, and then freeze-dried.

Example A-7

16% Substituted Octyl Urethane-Linked Hyaluronic Acid Derivative 2.0 g quaternary ammonium salt of hyaluronic acid (molecular weight=1040K) was dissolved in 180 ml DMSO. 0.6 g octyl isocyanate and 6.2 µl Stannous Octoate and 15.6 mg of 1,4-diazabicyclo[2,2,2]octane (catalyst) were added in sequence. The reaction was kept at 65° C. for 16 hours and then quenched with DBA. The reaction mixture was dialyzed in a saturated sodium chloride aqueous solution with a dialysis membrane (MWCO=12,000-14,000), purified, exchanged from quaternary ammonium salt to sodium salt, and then freeze-dried.

Example A-8

17.7% Substituted Dodecyl Urethane-Linked Hyaluronic Acid Derivative (C12-HA)

2.0 g quaternary ammonium salt of hyaluronic acid (molecular weight=1040K) was dissolved in 180 ml DMSO. 0.82 g octyl isocyanate and 6.8 µl Stannous Octoate and 16.9 mg 1,4-diazabicyclo[2,2,2]octane (catalyst) were added in sequence. The reaction was kept at 65° C. for 16 hours and then quenched with DBA. The reaction mixture was dialyzed in a saturated sodium chloride aqueous solution with a dialysis membrane (MWCO=12,000-14,000), purified, exchanged from quaternary ammonium salt to sodium salt, and then freeze-dried.

Example A-9

100% Substituted Dodecyl Urethane-Linked Hyaluronic Acid Derivative (C12-HA)

0.35 g ($3.54 \times 10^{-3}$ meq) quaternary ammonium salt of hyaluronic acid prepared from Preparative Example 1 was dissolved in 100 ml DMSO. 0.75 g dodecyl isocyanate ($3.54 \times 10^{-3}$ meq) and 100 µl di-n-butyltin dilaurate (catalyst) were added in sequence. The reaction was kept at 65° C. for 8 hours and then quenched with DBA. The reaction mixture was dialyzed in a saturated sodium chloride aqueous solution with a dialysis membrane (MWCO=12,000-14,000), purified, exchanged from quaternary ammonium salt to sodium salt, and then freeze-dried.

Figure 9:
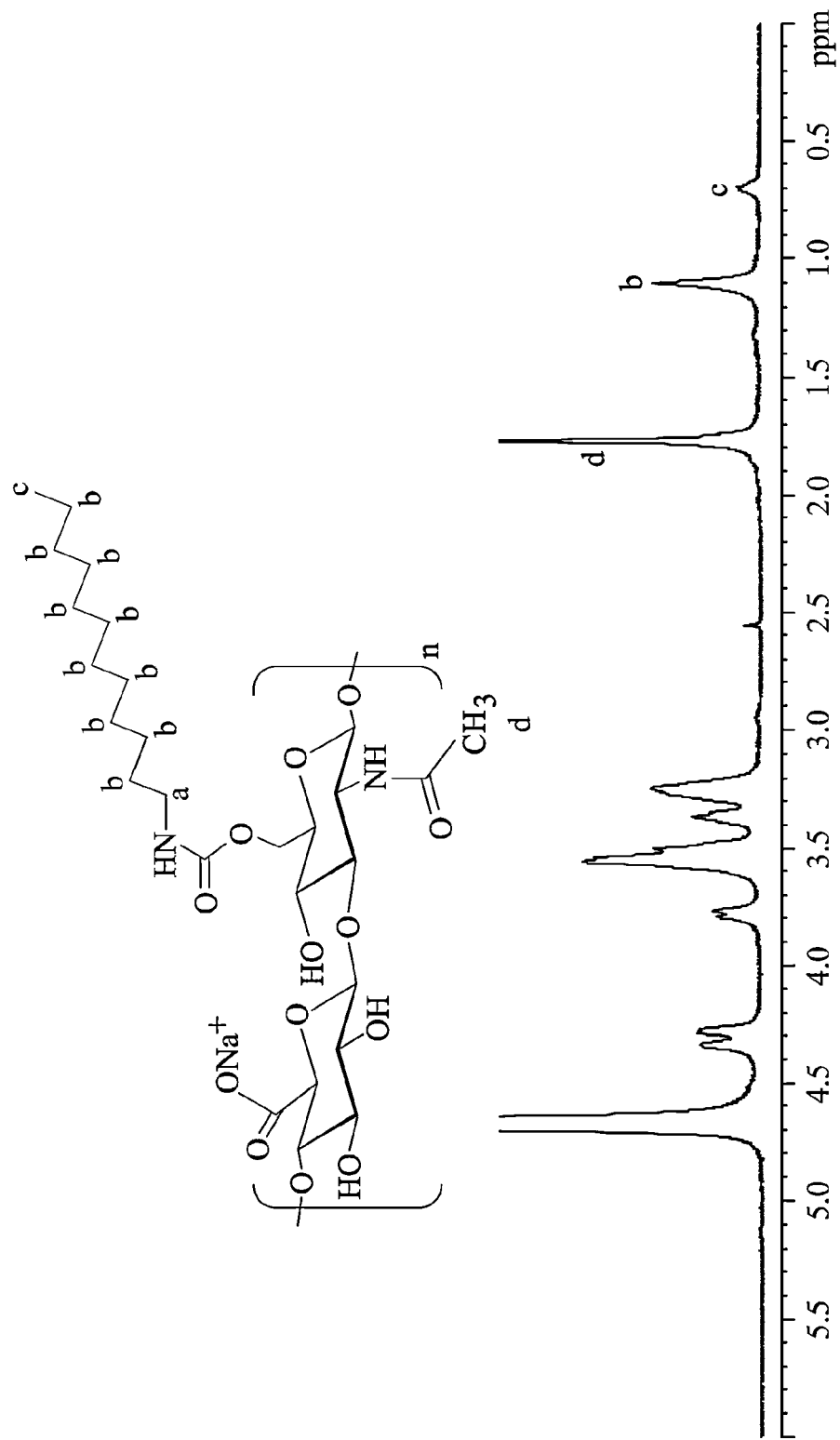
FIG. 9 shows the chemical structure of C12-HA, in which the protons on hydrocarbon group are labeled by b, c, and d, respectively.

FIG. 9 shows the chemical structure of C12-HA, in which the protons on hydrocarbon group are labeled by a, b, c, and d, respectively.

$^1$H NMR of C12-HA:
$\delta$=4.45~3.12 (m, hyaluronic backbone), 1.75 (s, H-12), 1.20~1.06 (m, H-b), 0.74~0.63 (m, H-c).

Example A-10

50% Substituted Dodecyl Urethane-Linked Hyaluronic Acid Derivative 0.35 g ($3.54 \times 10^{-3}$ meq) quaternary ammonium salt of hyaluronic acid prepared from Preparative Example 1 was dissolved in 100 ml DMSO. 0.375 g dodecyl isocyanate ($1.77 \times 10^{-3}$ meq) and 100 µl di-n-butyltin dilaurate (catalyst) were added in sequence. The reaction was kept at 65° C. for 8 hours and then quenched with DBA. The reaction mixture was dialyzed in a saturated sodium chloride aqueous solution with a dialysis membrane (MWCO=12,000-14,000), purified, exchanged from quaternary ammonium salt to sodium salt, and then freeze-dried.

Example A-11

10% Substituted Dodecyl Urethane-Linked Hyaluronic Acid Derivative 0.35 g ($3.54 \times 10^{-3}$ meq) quaternary ammonium salt of hyaluronic acid prepared from Preparative Example 1 was dissolved in 100 ml DMSO. 0.075 g dodecyl isocyanate ($3.54 \times 10^{-4}$ meq) and 100 µl di-n-butyltin dilaurate (catalyst) were added in sequence. The reaction was kept at 65° C. for 8 hours and then quenched with DBA. The reaction mixture was dialyzed in a saturated sodium chloride aqueous solution with a dialysis membrane (MWCO=12,000-14,000), purified, exchanged from quaternary ammonium salt to sodium salt, and then freeze-dried.

Series B Examples

Hyaluronic Acid Grafted with Prepolymer

Preparative Example 2

Synthesis of Mono-Functional Polycaprolactone (PCL)

Figure 6A:
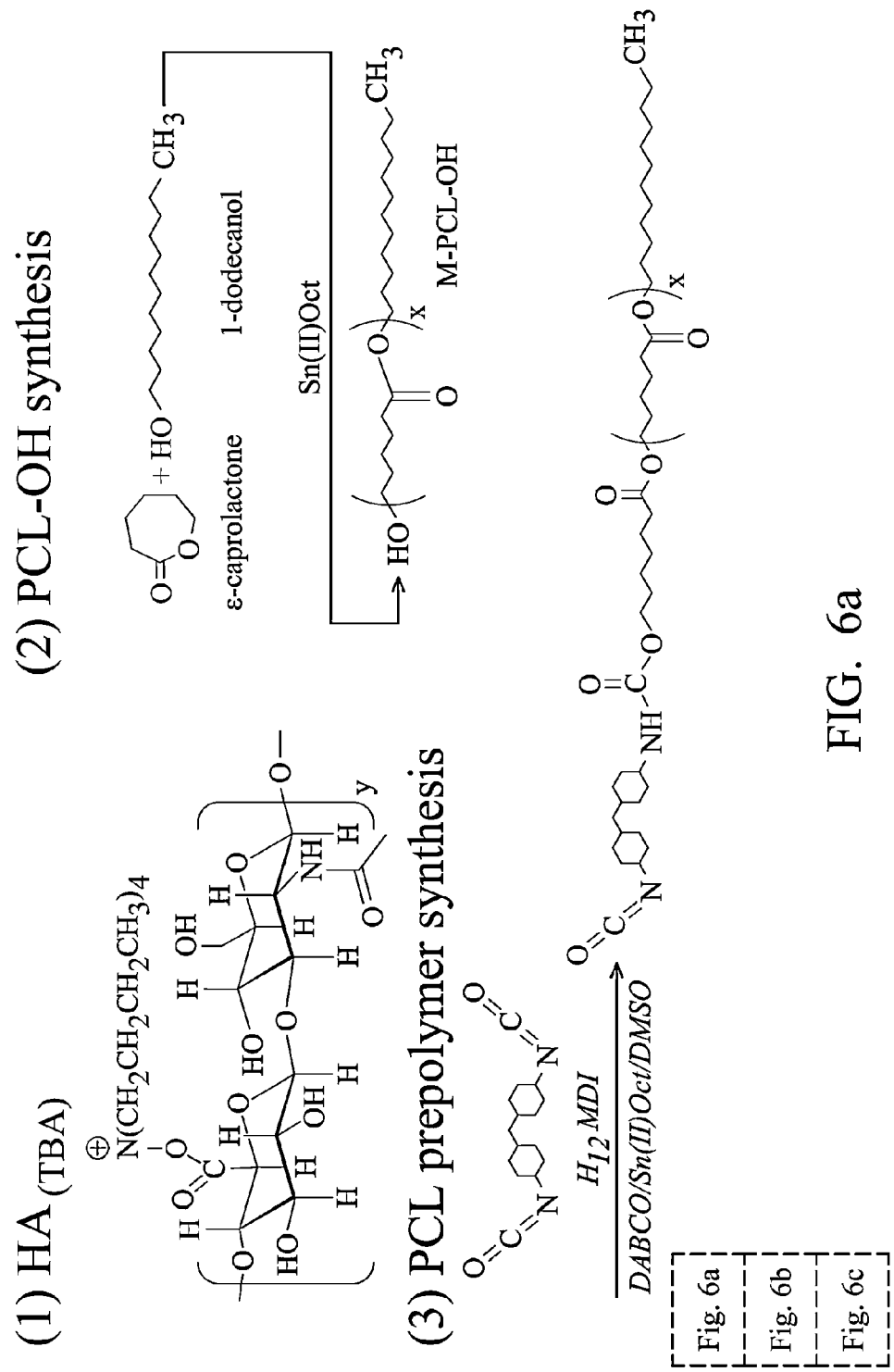
FIGS. 6a-6c shows the synthetic pathway of preparing hyaluronic acid copolymer grafted with PCL prepolymer.
Figure 6B:
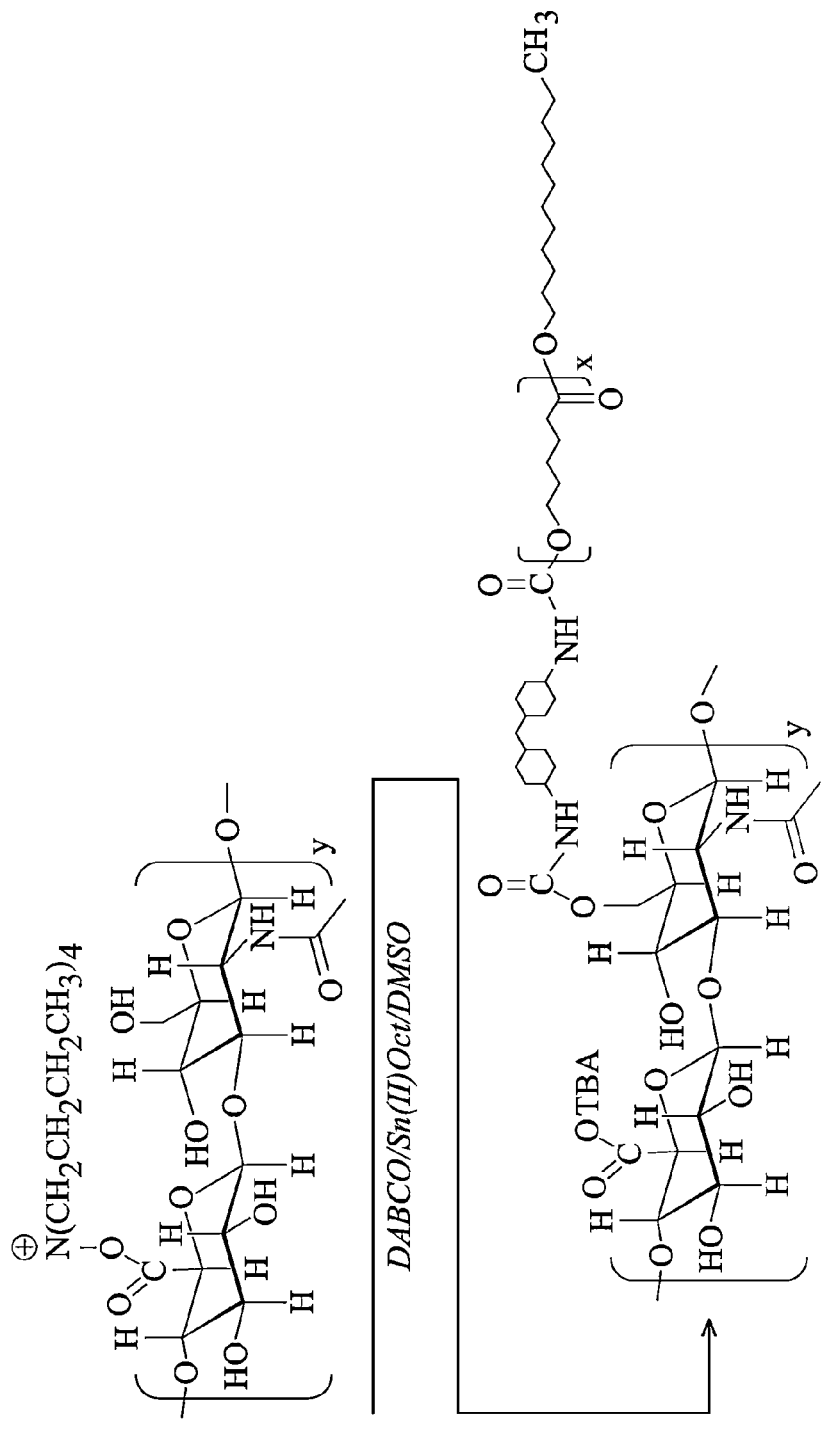
Figure 6C:
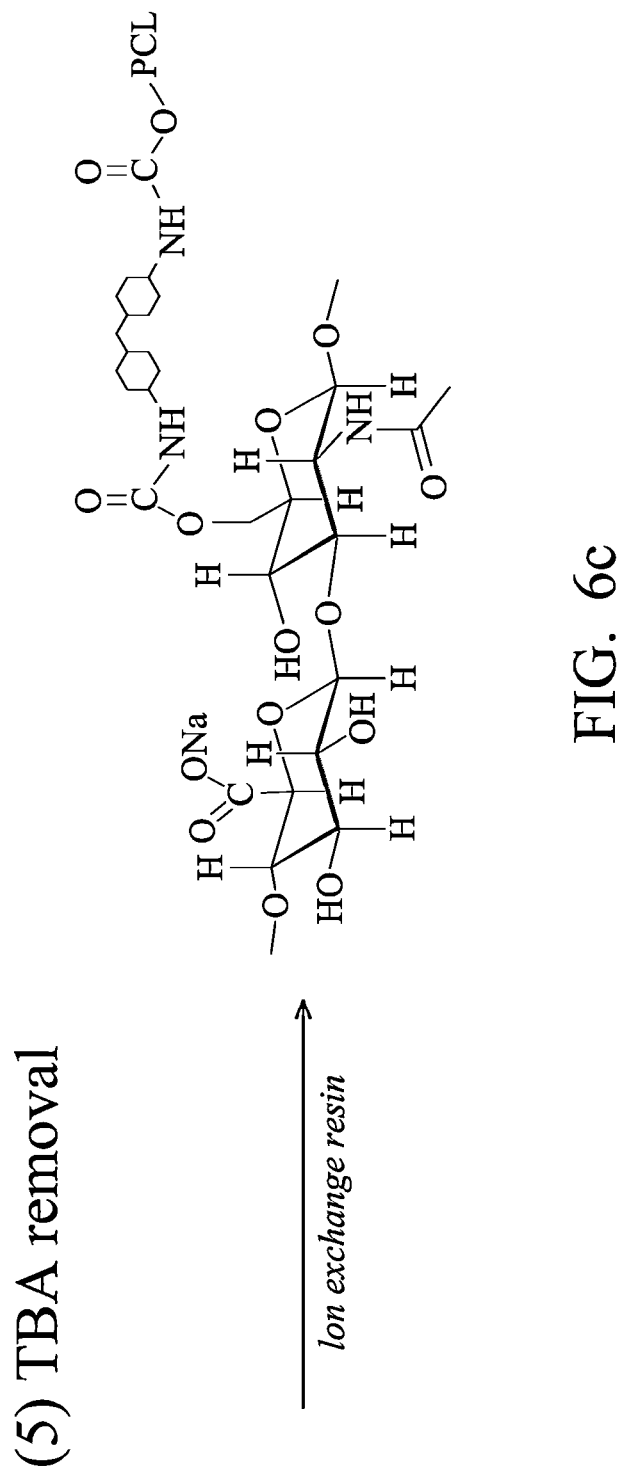

200 g (1.75 mole) caprolactone monomer was placed in a reaction vessel and 32.65 g (0.175 mole) 1-dodecanol (initiator) and 0.71 g ($1.75 \times 10^{-3}$ mole) stannous octanoate (catalyst) were then added. The reaction was kept at 120° C. for 2 hours. The reaction mixture was dissolved with chloroform and then purified by reprecipitation in ether. The synthetic pathway is shown in FIGS. 6a-6c and the repeating number in this figure, taking for an example, is 2. The GPC (gel permeation chromatography) analysis shows that Mn is 2352, Mw is 3012, and PDI (Mw/Mn) is 1.28.

Figure 10:
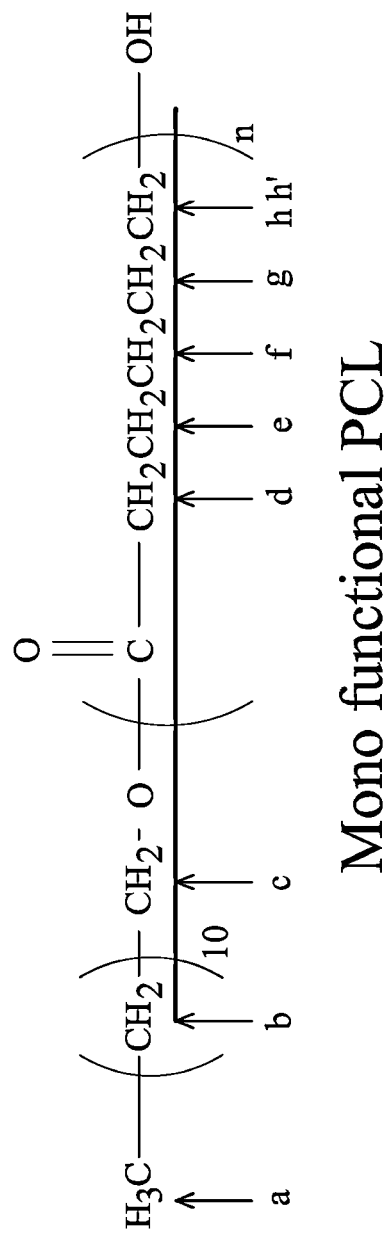
FIG. 10 shows the chemical structure of mono-functional PCL, in which protons are at the positions labeled by a, b, c, d, e, f, g, h and h', respectively.

FIG. 10 shows the chemical structure of mono-functional PCL, in which hydrogen positions are labeled a, b, c, d, e, f, g, h and h'.

NMR Data: PCL:

δ 0.76 (t, J=7.0 Hz, H-a), 1.16 (S, H-b), 3.96 (t, J=6.8 Hz, H-c), 2.20 (t, J=7.4 $H_z$, H-d), 1.56 (m, H-e, g), 1.30 (m, H-f), 3.96 (t, J=6.8$H_z$, H-h), 3.53 (t, J=7.0 Hz, H-h').

Preparative Example 3

Synthesis of Mono-Functional Poly L-Lactide (PLLA)

200 g (1.39 mole) lactide monomer was placed in a reaction vessel and 25.82 g (0.139 mole) 1-dodecanol (initiator) and 0.562 g ($1.39 \times 10^{-3}$ mole) of stannous octanoate (catalyst) were then added. The reaction was kept at 120° C. for 2 hours. The reaction mixture was dissolved with chloroform and then purified by reprecipitation in ether. The GPC analysis shows that Mn is 2189, Mw is 2797, and PDI (Mw/Mn) is 1.28.

Figure 11:
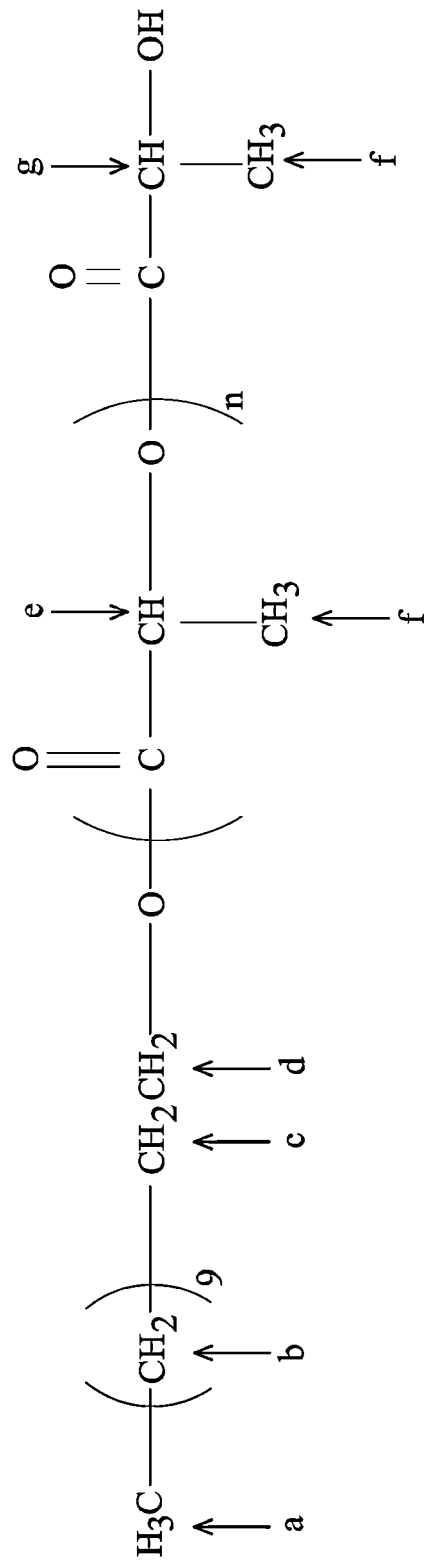
FIG. 11 shows the chemical structure of mono-functional PLLA, in which protons are at the positions labeled by a, b, c, d, e, f, and g, respectively.

FIG. 11 shows the chemical structure of mono-functional PLLA, in which hydrogen positions are labeled a, b, c, d, e, f, and g.

NMR Data:

PLLA: δ 0.76 (t, J=7.0$H_z$, H-a), 1.14 (S, H-b), 1.38 (m, H-c), 4.01 (m, H-d), 5.06 (m, H-e), 1.47 (d, J=7.2$H_z$, H-f), 4.24 (m, H-g).

Preparative Example 4

Synthesis of Poly Caprolactone3000-Poly Ethylene Glycol550 ($PCL_{3000}$-$PEG_{550}$) Copolymer 55.0 g Methoxy poly ethylene glycol (Mw=550) was placed in a reaction vessel and 88.6 ml of ε-caprolactone monomer and 0.6 ml stannous octanoate (catalyst) were then added. The reaction was kept at 130° C. for 8 hours. The reaction mixture was dissolved with methylene chloride and then purified by reprecipitation in ether. The GPC analysis shows that Mn is 2874, Mw is 3477, and PDI (Mw/Mn) is 1.21.

Preparative Example 5

Synthesis of Poly Caprolactone3000-Poly Ethylene Glycol1900 ($PCL_{3000}$-$PEG_{1900}$) Copolymer 60.0 g Methoxy poly ethylene glycol (Mw=1900) was placed in a reaction vessel and 63.0 ml of ε-caprolactone monomer and 0.5 ml stannous octanoate (catalyst) were then added. The reaction was kept at 130° C. for 8 hours. The reaction mixture was dissolved with methylene chloride and then purified by reprecipitation in ether. The GPC analysis shows that Mn is 3883, Mw is 4928, and PDI (Mw/Mn) is 1.27.

Example B-1

Synthesis of Hyaluronic Acid Copolymer Grafted with PCL Prepolymer ($HA_{220,000}$-g-100%-$PCL_{2,300}$ Copolymer)

5.75 g ($2.5 \times 10^{-3}$ mole) mono-functional PCL (M-PCL-OH) (Mw=2300) prepared from Preparative Example 2 was dissolved in 50 ml NMP, and then 0.42 g hexamethylene diisocyanate ($H_{12}$MDI) ($2.5 \times 10^{-3}$ mole) and 100 μl di-n-butyltin dilaurate were added in sequence. The reaction was kept at 60° C. for 5 hours. 1 g ($2.5 \times 10^{-3}$ mole) quaternary ammonium salt of hyaluronic acid (Mw=220,000) was dissolved in 150 ml DMSO and added to the PCL solution, followed by addition of 100 μl di-n-butyltin dilaurate. The reaction was kept at 60° C. for 12 hours and then quenched with DBA to deliver $HA_{220,000}$-g-100%-$PCL_{2,300}$ copolymer. The reaction mixture was purified in a saturated sodium chloride aqueous solution with a dialysis membrane (MWCO=3500). The copolymer was eluted through a ion-exchange resin to replace quaternary ammonium ion to sodium ion, and then freeze-dried. The synthetic pathway is shown in FIGS. 6a-6c.

Figure 12:
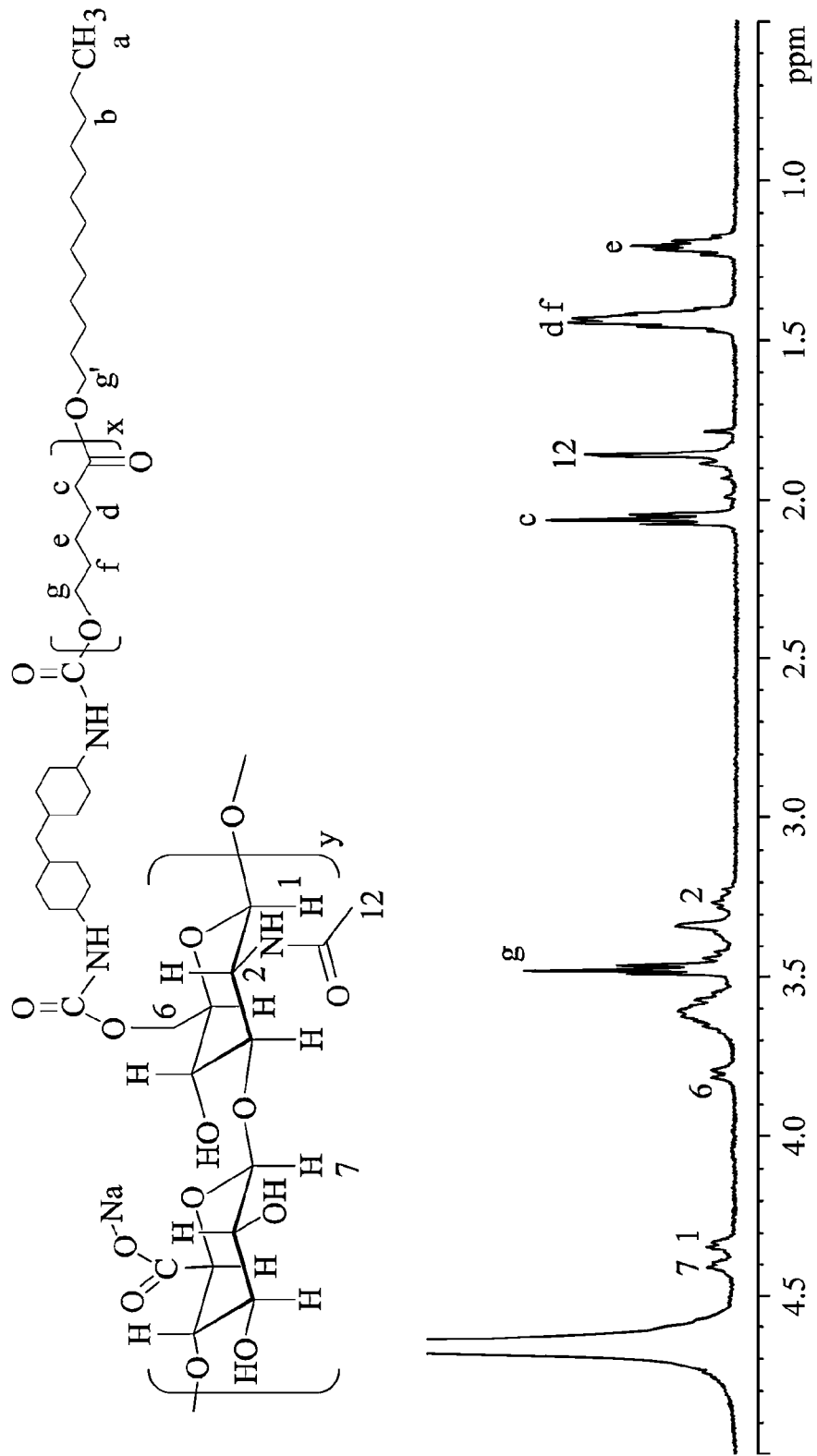
FIG. 12 shows the chemical structure of HA-graft-PCL and 1H NMR spectral assignments, in which hydrogens are at the positions labeled by a, b, c, d, e, f, g, and g' respectively.

FIG. 12 shows the chemical structure of HA-graft-PCL, and $^1$H NMR spectral assignments.

Figure 7:
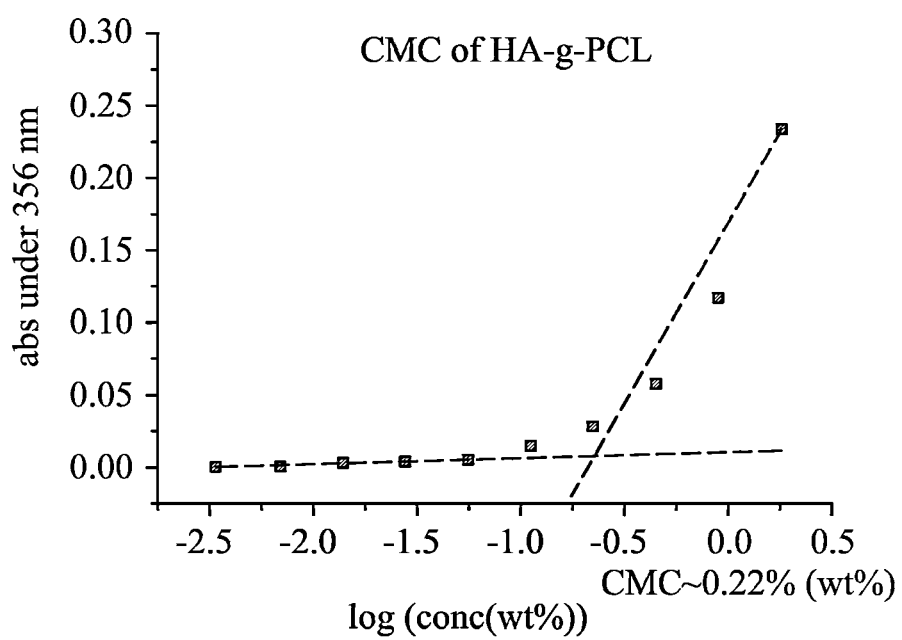
FIG. 7 shows the result of critical micelle concentration (CMC) determination for hyaluronic acid copolymer grafted with PCL prepolymer prepared from Example B-1.

Determination of Critical Micelle Concentration (CMC):

The $HA_{220,000}$-g-100%-$PCL_{2,300}$ copolymer was dissolved in 4 μM diphenyl hexatriene (DPH) solution at a concentration of 0.001%, 0.005%, 0.01%, 0.025%, 0.05%, 0.1%, 0.5%, and 1% respectively. Absorbance at 356 nm wavelength was measured with UV-VIS spectrometer. The result was shown in FIG. 7 and the CMC was 0.22 wt %.

Example B-2

Synthesis of Hyaluronic Acid Copolymer Grafted with PCL Prepolymer ($HA_{220,000}$-g-10%-$PCL_{2,300}$ Copolymer)

0.58 g ($2.5 \times 10^{-4}$ mole) mono-functional PCL (Mw=2300) was dissolved in 50 ml NMP, and then 0.042 g hexamethylene diisocyanate ($H_{12}$MDI)($2.5 \times 10^{-4}$ mole) and 100 μl di-n-butyltin dilaurate were added in sequence. The reaction was kept at 60° C. for 5 hours. 1 g ($2.5 \times 10^{-3}$ mole) quaternary ammonium salt of hyaluronic acid (Mw=220,000) was dissolved in 150 ml DMSO and added to the PCL solution, followed by addition of 100 μl di-n-butyltin dilaurate. The reaction was kept at 60° C. for 12 hours and then quenched with DBA to obtain $HA_{220,000}$-g-10%-$PCL_{2,300}$ copolymer. The reaction mixture was purified in a saturated sodium chloride aqueous solution with a dialysis membrane (MWCO=3500). The copolymer was eluted through an ion-exchange resin to replace quaternary ammonium ion to sodium ion, and then freeze-dried.

NMR data of HA-PCL:

δ 4.58 (m, H-1), 4.49 (m, H-1'), 4.07 (m, H-2), 3.21 (m, H-2'), 3.94 (m, H-3), 3.60 (m, H-3'), 3.52 (m, H-4), 3.60 (m, H-4'), 3.36 (m, H-5), 3.52 (m, H-5'), 4.16 (m, H-6a), 3.92 (m, H-6b), 2.28 (m, H-f), 3.90 (m, H-b), 1.60 (m, H-c, e), 1.45 (m, H-d), 3.89 (m, H-g), 1.40 (m, H-h), 0.86 (m, H-i), 2.03 (s, H-k).

Cytotoxicity Test:

L929-mouse fibroblast cell line was cultured in a 24-well plate at a density of $1 \times 10^5$ cell/ml at 37° C. in a humidified 5% $CO_2$/air incubator. After 24 hours, a confluent monolayer was formed.

UV-sterilized HA-PCL copolymer (10% grafting ratio) powder was dissolved in the culture medium to prepare various solutions with concentration ranging from $10^{-5}$ up to $10^{-2}$ g/ml.

Culture medium was removed and then 2 ml of the various HA-PCL-containing medium was added following continuous exposure for 1 day. The cell viability was analyzed by the MTT colorimetric assay. The results show that the HA-PCL copolymer micelles at various concentrations had no cytotoxicity response.

The MTT chlorimetric assay: Culture medium was removed and then washed three times with PBS (phosphate buffered saline). 5 mg/ml MTT was added to each well and then incubated at 37° C. for 3 hours. An equal volume of blocking solution (DMSO:SDS:medium (1:1:1)) was added for another 20 minutes. The fluid content of each well was transferred to the testing cuvette. The absorbances were measured at 560 nm wavelength. A higher absorbance indicates a higher viability.

Determination of Critical Micelle Concentration (CMC):
The $HA_{220,000}$-g-10%-$PCL_{2,300}$ copolymer was dissolved in 4 μM diphenyl hexatriene (DPH) solution at a concentration of 0.001%, 0.005%, 0.01%, 0.025%, 0.05%, 0.1%, 0.5%, and 1% respectively. Absorbance at 356 nm wavelength was measured with UV-VIS spectrometer. The CMC was 0.0851 wt %.

Example B-3

Synthesis of Hyaluronic Acid Copolymer Grafted with PCL Prepolymer ($HA_{50,000}$-g-20%-$PCL_{10,000}$ Copolymer)

1 g ($1 \times 10^{-4}$ mole) mono-functional PCL (Mw=10000) was dissolved in 100 ml NMP, and then 0.017 g hexamethylene diisocyanate ($1 \times 10^{-4}$ mole) and 100 μl di-n-butyltin dilaurate were added in sequence. The reaction was kept at 60° C. for 5 hours. 0.2 g ($2.5 \times 10^{-3}$ mole) quaternary ammonium salt of hyaluronic acid (Mw=50,000) was dissolved in 100 ml DMSO and added to the PCL solution, followed by addition of 100 μl di-n-butyltin dilaurate. The reaction was kept at 60° C. for 12 hours and then quenched with DBA to afford $HA_{50,000}$-g-20%-$PCL_{10,000}$ copolymer. The reaction mixture was purified in a saturated sodium chloride aqueous solution with a dialysis membrane (MWCO=3500). The copolymer was eluted through a ion-exchange resin to replace quaternary ammonium ion to sodium ion, and then freeze-dried.

NMR data of HA-PCL:
δ 4.58 (m, H-1), 4.49 (m, H-1'), 4.07 (m, H-2), 3.21 (m, H-2'), 3.94 (m, H-3), 3.60 (m, H-3'), 3.52 (m, H-4), 3.60 (m, H-4'), 3.36 (m, H-5), 3.52 (m, H-5'), 4.16 (m, H-6a), 3.92 (m, H-6b), 2.28 (m, H-f), 3.90 (m, H-b), 1.60 (m, H-c, e), 1.45 (m, H-d), 3.89 (m, H-g), 1.40 (m, H-h), 0.86 (m, H-i), 2.03 (s, H-k).

Example B-4

Synthesis of Hyaluronic Acid Copolymer Grafted with PCL Prepolymer ($HA_{50,000}$-g-100%-$PCL_{2,300}$ Copolymer)

1.15 g ($5 \times 10^{-4}$ mole) mono-functional PCL (Mw=2300) was dissolved in 50 ml NMP, and then 0.084 g hexamethylene diisocyanate ($5 \times 10^{-4}$ mole) and 100 μl di-n-butyltin dilaurate were added in sequence. The reaction was kept at 60° C. for 5 hours. 0.2 g ($5 \times 10^{-4}$ mole) quaternary ammonium salt of hyaluronic acid (Mw=50,000) was dissolved in 100 ml DMSO and added to the PCL solution, followed by addition of 100 μl di-n-butyltin dilaurate. The reaction was kept at 60° C. for 12 hours and then quenched with DBA to generate $HA_{50,000}$-g-100%-$PCL_{2,300}$ copolymer. The reaction mixture was purified in a saturated sodium chloride aqueous solution with a dialysis membrane (MWCO=3500). The copolymer was eluted through a ion-exchange resin to replace quaternary ammonium ion to sodium ion, and then freeze-dried.

Determination of Critical Micelle Concentration (CMC):
The $HA_{50,000}$-g-100%-$PCL_{2,300}$ copolymer was dissolved in 4 μM diphenyl hexatriene (DPH) solution at a concentration of 0.001%, 0.005%, 0.01%, 0.025%, 0.05%, 0.1%, 0.5%, and 1% respectively. Absorbance at 356 nm wavelength was measured with UV-VIS spectrometer. The CMC was 0.0794 wt %.

Example B-5

Synthesis of Hyaluronic Acid Copolymer Grafted with PCL Prepolymer ($HA_{220,000}$-g-100%-$PLLA_{2,300}$ Copolymer)

5.75 g ($2.5 \times 10^{-3}$ mole) mono-functional PLLA (Mw=2300) was dissolved in 50 ml NMP, and then 0.42 g hexamethylene diisocyanate ($2.5 \times 10^{-3}$ mole) and 100 μl di-n-butyltin dilaurate were added in sequence. The reaction was kept at 60° C. for 5 hours. 1 g ($2.5 \times 10^{-3}$ mole) quaternary ammonium salt of hyaluronic acid (Mw=220,000) was dissolved in 150 ml DMSO and added to the PLLA solution, followed by addition of 100 μl di-n-butyltin dilaurate. The reaction was kept at 60° C. for 12 hours and then quenched with DBA to obtain $HA_{220,000}$-g-100%-$PLLA_{2,300}$ copolymer. The reaction mixture was purified in a saturated sodium chloride aqueous solution with a dialysis membrane (MWCO=3500). The copolymer was eluted through an ion-exchange resin to replace quaternary ammonium ion to sodium ion, and then freeze-dried.

Figure 13:
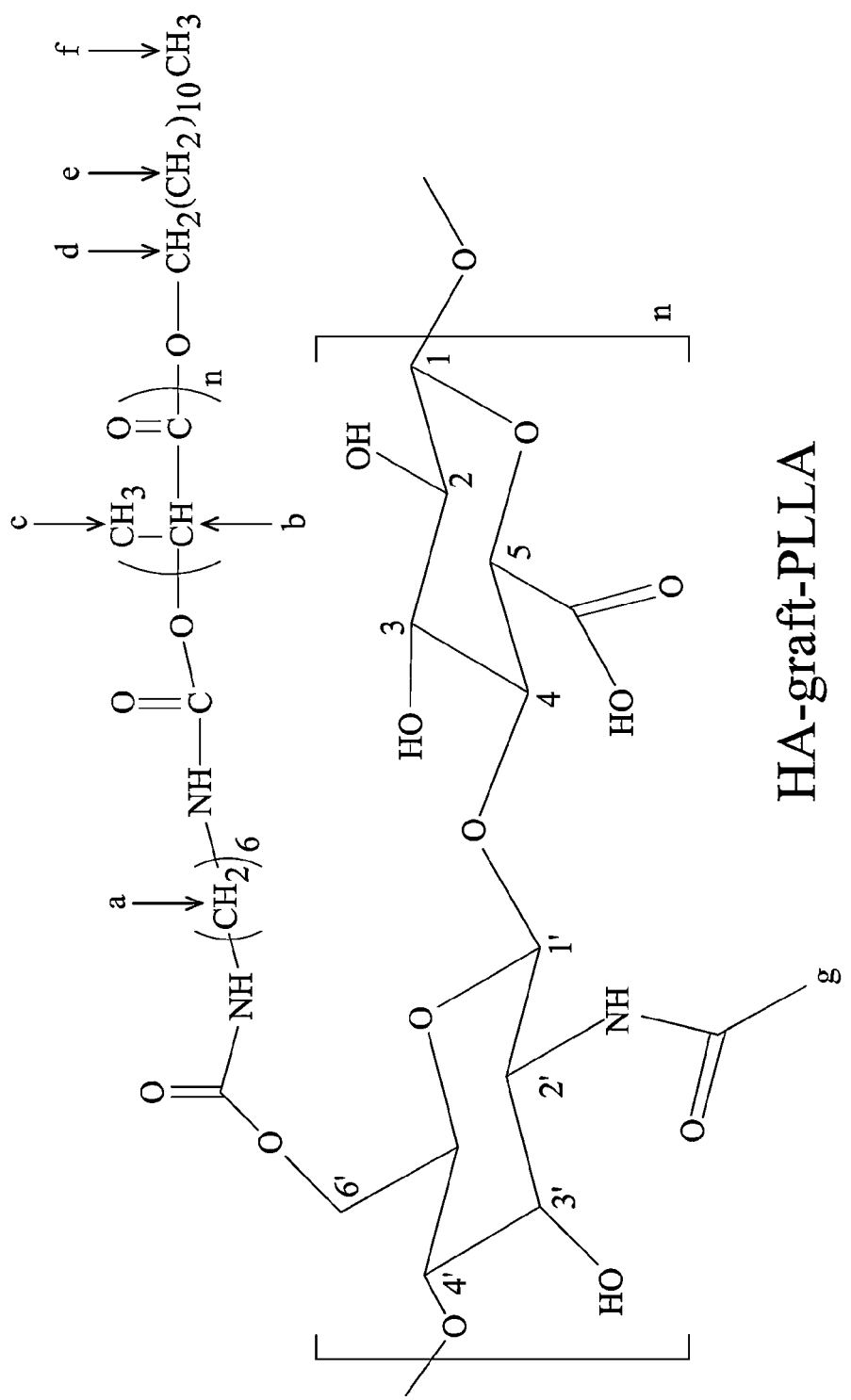
FIG. 13 shows the chemical structure of HA-graft-PLLA, in which protons are at the positions labeled by a, b, c, d, e and f, respectively.

FIG. 13 shows the chemical structure of HA-graft-PLLA, in which hydrogen positions are labeled a, b, c, d, e, f, and g.

NMR data of HA-PLLA:
δ 4.59 (m, H-1), 4.50 (m, H-1'), 4.07 (m, H-2), 3.22 (m, H-2'), 3.94 (m, H-3), 3.60 (m, H-3'), 3.52 (m, H-4), 3.60 (m, H-4'), 3.37 (m, H-5), 3.52 (m, H-5'), 4.16 (m, H-6a), 3.92 (m, H-6b), 1.65 (m, H-a), 5.02 (m, H-b), 1.47 (d, J=7.2$H_Z$, H-c), 4.01 (m, H-d), 1.15 (S, H-e), 0.76 (t, J=7.0$H_Z$, H-f), 2.13 (s, H-g).

Example B-6

Synthesis of Hyaluronic Acid Copolymer Grafted with PCL Prepolymer ($HA_{20,000}$-g-100%-$PCL_{2,300}$ Copolymer)

1.15 g ($5 \times 10^{-4}$ mole) mono-functional PCL (Mw=2300) was dissolved in 50 ml NMP, and then 0.084 g hexamethylene diisocyanate ($5 \times 10^{-4}$ mole) and 100 μl di-n-butyltin dilaurate were added in sequence. The reaction was kept at 60° C. for 5 hours. 0.2 g ($5 \times 10^{-4}$ mole) quaternary ammonium salt of hyaluronic acid (Mw=20,000) was dissolved in 100 ml DMSO and added to the PCL solution, followed by addition of 100 μl di-n-butyltin dilaurate. The reaction was kept at 60° C. for 12 hours and then quenched with DBA to provide $HA_{20,000}$-g-100%-$PCL_{2,300}$ copolymer. The reaction mixture was purified in a saturated sodium chloride aqueous solution with a dialysis membrane (MWCO=3500). The copolymer was eluted through an ion-exchange resin to replace quaternary ammonium ion to sodium ion, and then freeze-dried.

Determination of Critical Micelle Concentration (CMC):

The $HA_{20,000}$-g-100%-$PCL_{2,300}$ copolymer was dissolved in 4 μM diphenyl hexatriene (DPH) solution at a concentration of 0.001%, 0.005%, 0.01%, 0.025%, 0.05%, 0.1%, 0.5%, and 1% respectively. Absorbance at 356 nm wavelength was measured with UV-VIS spectrometer. The CMC was 0.432 wt %.

Example B-7

Synthesis of Hyaluronic Acid Copolymer Grafted with PCL Prepolymer ($HA_{20,000}$-g-50%-$PCL_{2,300}$ Copolymer)

0.58 g ($2.5 \times 10^{-4}$ mole) mono-functional PCL (Mw=2300) was dissolved in 50 ml NMP, and then 0.042 g hexamethylene diisocyanate ($2.5 \times 10^{-4}$ mole) and 100 μl di-n-butyltin dilaurate were added in sequence. The reaction was kept at 60° C. for 5 hours. 0.2 g ($5 \times 10^{-4}$ mole) quaternary ammonium salt of hyaluronic acid (Mw=50,000) was dissolved in 100 ml DMSO and added to the PCL solution, followed by addition of 100 μl di-n-butyltin dilaurate. The reaction was kept at 60° C. for 12 hours and then quenched with DBA to give $HA_{20,000}$-g-50%-$PCL_{2,300}$ copolymer. The reaction mixture was purified in a saturated sodium chloride aqueous solution with a dialysis membrane (MWCO=3500). The copolymer was eluted through an ion-exchange resin to replace quaternary ammonium ion to sodium ion, and then freeze-dried.

Determination of Critical Micelle Concentration (CMC):

The $HA_{20,000}$-g-50%-$PCL_{2,300}$ copolymer was dissolved in 4 μM diphenyl hexatriene (DPH) solution at a concentration of 0.001%, 0.005%, 0.01%, 0.025%, 0.05%, 0.1%, 0.5%, and 1% respectively. Absorbance at 356 nm wavelength was measured with UV-VIS spectrometer. The CMC was 0.255 wt %.

Example B-8

Synthesis of Hyaluronic Acid Copolymer Grafted with PCL-PEG Prepolymer [$HA_{16,000}$-g-10% ($PCL_{3000}$-$PEG_{550}$)Copolymer]

1.87 g ($5.4 \times 10^{-4}$ mole) $PEL_{3000}$-$PEG_{550}$ copolymer was dissolved in 4 ml DMSO. 5 μl Stannous Octoate and 12 mg 1,4-diazabicyclo[2.2.2]octane were dissolved in 2 ml DMSO and added to the PEG-PCL copolymer solution. And then 0.12 ml 1-isocyanato-4-[(4-isocyanatocyclohexyl)methyl]cyclohexane ($4.8 \times 10^{-4}$ mole) was added to the reaction mixture. The reaction was kept at 60° C. for 6 hours. 3.0 g ($4.84 \times 10^{-3}$ mole) quaternary ammonium salt of hyaluronic acid (Mw=16,000) was dissolved in 13 ml DMSO. 11.5 μl Stannous Octoate and 29.0 mg 1,4-diazabicyclo[2,2,2]octane were dissolved in 2 ml DMSO and added to the quaternary ammonium salt of hyaluronic acid solution. The PEG-PCL prepolymer solution was added to the quaternary ammonium salt of hyaluronic acid solution. The reaction was kept at 60° C. for 16 hours and then quenched with DBA to obtain $HA_{16,000}$-g-10%($PCL_{3,000}$-$PEG_{550}$) copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Determination of Critical Micelle Concentration (CMC):

The $HA_{16,000}$-g-10%($PCL_{3000}$-$PEG_{550}$) copolymer was dissolved in $1.8 \times 10^{-4}$ M pyrene solution at a concentration of 0.0004%, 000781%, 0.00156%, 0.00313%, 0.00625%, 0.0125%, 0.025%, 0.05%, and 0.1% respectively. Emission at 390 nm wavelength was measured with Photoluminenscence spectrometer, the CMC was 0.0021 wt %.

Determination of Micelle Particle Size:

The size of the $HA_{16,000}$-g-10%($PCL_{3000}$-$PEG_{550}$) micelles in aqueous solution was determined using a DLS analyzer at 25° C. The mean diameter of the $HA_{16,000}$-g-10% ($PCL_{3000}$-$PEG_{550}$) micelles measured using the analyzer was 164 nm.

Example B-9

Synthesis of Hyaluronic Acid Copolymer Grafted with PCL-PEG Prepolymer [$HA_{16,000}$-g-20% ($PCL_{3000}$-$PEG_{550}$) Copolymer]

3.74 g ($1.08 \times 10^{-3}$ mole) $PEL_{3000}$-$PEG_{550}$ copolymer was dissolved in 12 ml DMSO. 10 μl Stannous Octoate and 24 mg 1,4-diazabicyclo[2.2.2]octane were dissolved in 2 ml DMSO and added to the PEG-PCL copolymer solution. 0.25 mL of 1-isocyanato-4-[(4-isocyanatocyclohexyl)methyl]cyclohexane ($9.7 \times 10^{-4}$ mole) was added to the resulting mixture and the reaction was kept at 60° C. for 6 hours. 3.0 g ($4.84 \times 10^{-3}$ mole) quaternary ammonium salt of hyaluronic acid (Mw=16,000) was dissolved in 15 ml DMSO. 15.9 μl Stannous Octoate and 40 mg 1,4-diazabicyclo[2,2,2]octane were dissolved in 2 ml DMSO and added to the quaternary ammonium salt of hyaluronic acid solution. The PEG-PCL prepolymer solution was added to the quaternary ammonium salt of hyaluronic acid solution. The reaction was kept at 60° C. for 16 hours and then quenched with DBA to obtain $HA_{16,000}$-g-20% $PCL3,000$-$PEG_{550}$ copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Determination of Critical Micelle Concentration (CMC):

The $HA_{16,000}$-g-20%($PCL_{3000}$-$PEG_{550}$) copolymer was dissolved in $1.8 \times 10^{-4}$ M pyrene solution at a concentration of 0.0004%, 000781%, 0.00156%, 0.00313%, 0.00625%, 0.0125%, 0.025%, 0.05%, and 0.1% respectively. Emission at 390 nm wavelength was measured with Photoluminenscence spectrometer, the CMC was 0.000782 wt %.

Determination of Micelle Particle Size:

The size of the $HA_{16,000}$-g-10%($PCL_{3000}$-$PEG_{550}$) micelles in aqueous solution was determined using a DLS analyzer at 25° C. The mean diameter of the $HA_{16,000}$-g-20% ($PCL_{3000}$-$PEG_{550}$) micelles measured using the analyzer was 155 nm.

Example B-10

Synthesis of Hyaluronic Acid Copolymer Grafted with PCL-PEG prepolymer [$HA_{16,000}$-g-6% ($PCL_{3000}$-$PEG_{1900}$) Copolymer]

1.06 g ($2.2 \times 10^{-4}$ mole) $PCL_{3000}$-$PEG_{1900}$ copolymer was dissolved in 2 ml DMSO. 3 μl Stannous Octoate and 7 mg 1,4-diazabicyclo[2.2.2]octane were dissolved in 2 ml DMSO and added to the PEG-PCL copolymer solution. 0.05 mL 1-isocyanato-4-[(4-isocyanatocyclohexyl)methyl]cyclohexane ($1.9 \times 10^{-4}$ mole) was added to the resulting mixture and the reaction was kept at 60° C. for 6 hours. 2.0 g ($3.23 \times 10^{-3}$ mole) of quaternary ammonium salt of hyaluronic acid (Mw=16,000) was dissolved in 16 ml DMSO. 7.2 μl Stannous Octoate and 18 mg 1,4-diazabicyclo[2,2,2]octane were dissolved in 2 ml DMSO and added to the quaternary ammonium salt of hyaluronic acid solution. The PEG-PCL prepolymer solution was added to the quaternary ammonium salt of hyaluronic acid solution. The reaction was kept at 60° C. for 16 hours and then quenched with DBA to obtain $HA_{16,000}$-g-10%($PCL_{3,000}$-$PEG_{1900}$) copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Example B-11

Synthesis of Hyaluronic Acid Copolymer Grafted with PCL-PEG Prepolymer [$HA_{16,000}$-g-20% ($PCL_{3000}$-$PEG_{1900}$) Copolymer]

3.53 g ($7.2 \times 10^{-4}$ mole) $PCL_{3000}$-$PEG_{1900}$ copolymer was dissolved in 2 ml DMSO. 9 µl Stannous Octoate and 22 mg 1,4-diazabicyclo[2.2.2]octane were dissolved in 2 ml DMSO and added to the PEG-PCL copolymer solution. 0.17 mL 1-isocyanato-4-[(4-isocyanatocyclohexyl)methyl]cyclohexane ($6.5 \times 10^{-4}$ mole) was added to the resulting mixture and the reaction was kept at 60° C. for 6 hours. 2.0 g ($3.23 \times 10^{-3}$ mole) quaternary ammonium salt of hyaluronic acid (Mw=16,000) was dissolved in 11 ml DMSO. 12.8 µl Stannous Octoate and 32 mg 1,4-diazabicyclo[2,2,2]octane were dissolved in 2 ml DMSO and added to the quaternary ammonium salt of hyaluronic acid solution. The PEG-PCL prepolymer solution was added to the quaternary ammonium salt of hyaluronic acid solution. The reaction was kept at 60° C. for 16 hours and then quenched with DBA to obtain $HA_{16,000}$-g-20%($PCL_{3,000}$-$PEG_{1900}$) copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Example B-12

Synthesis of Hyaluronic Acid Copolymer Grafted with PEG Prepolymer $HA_{1,040,000}$-g-100% $PEG_{550}$ Copolymer 1.97 g ($3.58 \times 10^{-3}$ mole) methoxy polyethylene glycols (Mw=550) was dissolved in 5 ml DMSO. 4.7 µl Stannous Octoate and 11.82 mg 1,4-diazabicyclo[2.2.2]octane were dissolved in 2 ml DMSO and added to the methoxy polyethylene glycols solution. 0.83 ml 1-isocyanato-4-[(4-isocyanatocyclohexyl)methyl]cyclohexane ($3.22 \times 10^{-3}$ mole) was added to the resulting mixture and the reaction was kept at 60° C. for 6 hours. 1.0 g ($1.613 \times 10^{-3}$ mole) quaternary ammonium salt of hyaluronic acid (Mw=1,000,000) was dissolved in 152 ml DMSO. 8.7 µl Stannous Octoate and 21.7 mg 1,4-diazabicyclo[2,2,2]octane were dissolved in 2 ml DMSO and added to the quaternary ammonium salt of hyaluronic acid solution. The PEG prepolymer solution was added to the quaternary ammonium salt of hyaluronic acid solution. The reaction was kept at 60° C. for 16 hours and then quenched with DBA to obtain $HA_{1,040,000}$-g-100% $PEG_{550}$ copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Example B-13

Synthesis of Hyaluronic Acid Copolymer Grafted with PEG Prepolymer $HA_{1,040,000}$-g-30% $PEG_{550}$ Copolymer 0.531 g ($9.66 \times 10^{-4}$ mole) methoxy polyethylene glycols (Mw=550) was dissolved in 1.3 ml DMSO. 1.4 µl Stannous Octoate and 3.6 mg 1,4-diazabicyclo[2,2,2]octane were dissolved in 1 ml DMSO and added to the methoxy polyethylene glycols solution. 0.22 mL 1-isocyanato-4-[(4-isocyanatocyclohexyl)methyl]cyclohexane ($8.69 \times 10^{-4}$ mole) was added to the resulting mixture and the reaction was kept at 60° C. for 6 hours. 2.0 g ($3.22 \times 10^{-3}$ mole) quaternary ammonium salt of hyaluronic acid (Mw=1,000,000) was dissolved in 98 ml DMSO. 6.2 µl Stannous Octoate and 15.6 mg of 1,4-diazabicyclo[2,2,2]octane were dissolved in 2 ml DMSO and added to the above quaternary ammonium salt of hyaluronic acid solution. The mPEG prepolymer solution was added to the quaternary ammonium salt of hyaluronic acid solution. The reaction was kept at 60° C. for 16 hours and then quenched with DBA to obtain $HA_{1,040,000}$-g-30% $PEG_{550}$ copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Example B-14

Synthesis of Hyaluronic Acid Copolymer Grafted with PEG Prepolymer $HA_{1,040,000}$-g-5% $PEG_{550}$ Copolymer 0.05 g ($9 \times 10^{-5}$ mole) of methoxy polyethylene glycols (Mw=550) was dissolved in 1 ml of DMSO. 1.4 µl Stannous Octoate and 3.7 mg of 1,4-diazabicyclo[2,2,2]octane were dissolved in 1 ml of DMSO and added to the above methoxy polyethylene glycols solution. And then 0.02 ml of 1-isocyanato-4-[(4-isocyanatocyclohexyl)methyl]cyclohexane ($8.1 \times 10^{-5}$ mole) was added to the above solution. The reaction temperature was 60° C. and the reaction time was 6 hours. After reaction, 1 g ($1.613 \times 10^{-3}$ mole) of quaternary ammonium salt of hyaluronic acid (Mw=1,040,000) was dissolved in 100 ml of DMSO. 1.7 µl of Stannous Octoate and 4.0 mg of 1,4-diazabicyclo[2,2,2]octane were dissolved in 2 ml of DMSO and added to the above quaternary ammonium salt of hyaluronic acid solution. And then the above mPEG prepolymer solution was added to the quaternary ammonium salt of hyaluronic acid solution. The reaction temperature was 60° C. After 16 hours of reaction, DBA was added to stop the reaction, obtaining $HA_{1,040,000}$-g-5% $PEG_{550}$ copolymer. The reaction mixture was dialyzed in a saturated sodium chloride aqueous solution with a dialysis membrane (MWCO=12,000-14,000), purified, exchanged from quaternary ammonium salt to sodium salt, and then freeze-dried.

Example B-15

Synthesis of Hyaluronic Acid Copolymer Grafted with PEG Prepolymer $HA_{1,040,000}$-g-100% $PEG_{5000}$ Copolymer 17.89 g ($3.58 \times 10^{-3}$ mole) methoxy polyethylene glycols (Mw=5000) was dissolved in 63 ml DMSO. 42.9 µl Stannous Octoate and 107.3 mg 1,4-diazabicyclo[2.2.2]octane were dissolved in 2 ml DMSO and added to the methoxy polyethylene glycols solution. And then 0.83 ml 1-isocyanato-4-[(4-isocyanatocyclohexyl)methyl]cyclohexane ($3.22\times10^{-3}$ mole) was added to the resulting mixture and the reaction was kept at 60° C. for 6 hours. 1.0 g ($1.613\times10^{-3}$ mole) of quaternary ammonium salt of hyaluronic acid (Mw=1,000,000) was dissolved in 189 ml DMSO. 43 µl Stannous Octoate and 107.8 mg 1,4-diazabicyclo[2,2,2]octane were dissolved in 2 ml DMSO and added to the quaternary ammonium salt of hyaluronic acid solution. The mPEG prepolymer solution was added to the quaternary ammonium salt of hyaluronic acid solution. The reaction was kept at 60° C. for 16 hours and then quenched with DBA to obtain $HA_{1,040,000}$-g-100% $PEG_{5000}$ copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Example B-16

Synthesis of Hyaluronic Acid Copolymer Grafted with PEG Prepolymer $HA_{1,040,000}$-g-6% $PEG_{5000}$ Copolymer 0.966 g ($1.93\times10^{-4}$ mole) methoxy polyethylene glycols (Mw=5000) was dissolved in 2.8 ml DMSO. 2.3 µl Stannous Octoate and 5.8 mg 1,4-diazabicyclo[2.2.2]octane were dissolved in 1 ml DMSO and added to the methoxy polyethylene glycols solution. 0.045 ml 1-isocyanato-4-[(4-isocyanatocyclohexyl)methyl]cyclohexane ($1.74\times10^{-4}$ mole) was added to the resulting mixture and the reaction was kept at 60° C. for 6 hours. 2.0 g ($3.22\times10^{-3}$ mole) quaternary ammonium salt of hyaluronic acid (Mw=1,000,000) was dissolved in 98 ml DMSO. 7.1 µl Stannous Octoate and 17.8 mg 1,4-diazabicyclo[2,2,2]octane were dissolved in 2 ml DMSO and added to the quaternary ammonium salt of hyaluronic acid solution. The mPEG prepolymer solution was added to the quaternary ammonium salt of hyaluronic acid solution. The reaction was kept at 60° C. for 16 hours and then quenched with DBA to obtain $HA_{1,040,000}$-g-6% $PEG_{5000}$ copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Example B-17

Synthesis of Hyaluronic Acid Copolymer Grafted with PEG Prepolymer $HA_{16,000}$-g-6% $PEG_{5000}$ Copolymer 0.966 g ($1.93\times10^{-4}$ mole) methoxy polyethylene glycols (Mw=5000) was dissolved in 2.8 ml DMSO. 2.3 µl Stannous Octoate and 5.8 mg 1,4-diazabicyclo[2.2.2]octane were dissolved in 1 ml DMSO and added to the methoxy polyethylene glycols solution. 0.045 ml 1-isocyanato-4-[(4-isocyanatocyclohexyl)methyl]cyclohexane ($1.74\times10^{-4}$ mole) was added to the resulting mixture and the reaction was kept at 60° C. for 6 hours. 2.0 g ($3.22\times10^{-3}$ mole) of quaternary ammonium salt of hyaluronic acid (Mw=16,000) was dissolved in 5.5 ml of DMSO. 7.1 µl Stannous Octoate and 17.8 mg 1,4-diazabicyclo[2,2,2]octane were dissolved in 2 ml DMSO and added to the quaternary ammonium salt of hyaluronic acid solution. The mPEG prepolymer solution was added to the quaternary ammonium salt of hyaluronic acid solution. The reaction was kept at 60° C. for 16 hours and then quenched with DBA to obtain $HA_{16,000}$-g-6% $PEG_{5000}$ copolymer. The reaction mixture was purified in a saturated sodium chloride aqueous solution with a dialysis membrane (MWCO=12,000-14,000). The copolymer was eluted through a ion-exchange resin to replace quaternary ammonium ion to sodium ion, and then freeze-dried.

Example B-18

Synthesis of Hyaluronic Acid Copolymer Grafted with PEG Prepolymer $HA_{100,000}$-g-6% $PEG_{5000}$ Copolymer 0.966 g ($1.93\times10^{-4}$ mole) methoxy polyethylene glycols (Mw=5000) was dissolved in 2.8 ml DMSO. 2.3 µl Stannous Octoate and 5.8 mg 1,4-diazabicyclo[2.2.2]octane were dissolved in 1 ml DMSO and added to the methoxy polyethylene glycols solution. 0.045 ml 1-isocyanato-4-[(4-isocyanatocyclohexyl)methyl]cyclohexane ($1.74\times10^{-4}$ mole) was added to the resulting mixture and the reaction was kept at 60° C. for 6 hours. 2.0 g ($3.22\times10^{-3}$ mole) quaternary ammonium salt of hyaluronic acid (Mw=100,000) was dissolved in 15 ml DMSO. 7.1 µl Stannous Octoate and 17.8 mg 1,4-diazabicyclo[2.2.2]octane were dissolved in 2 ml DMSO and added to the quaternary ammonium salt of hyaluronic acid solution. The mPEG prepolymer solution was added to the quaternary ammonium salt of hyaluronic acid solution. The reaction was kept at 60° C. for 16 hours and then quenched with DBA to obtain $HA_{1040000}$-g-6% $PEG_{5000}$ copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Example B-19

Synthesis of Hyaluronic Acid Copolymer Grafted with PEG Prepolymer $HA_{100,000}$-g-30% $PEG_{550}$ Copolymer 0.531 g ($9.66\times10^{-4}$ mole) methoxy polyethylene glycols (Mw=550) was dissolved in 1.3 ml DMSO. 1.4 µl Stannous Octoate and 3.6 mg 1,4-diazabicyclo[2.2.2]octane were dissolved in 1 ml DMSO and added to the methoxy polyethylene glycols solution. 0.22 mL 1-isocyanato-4-[(4-isocyanatocyclohexyl)methyl]cyclohexane ($8.69\times10^{-4}$ mole) was added to the resulting mixture and the reaction was kept at 60° C. for 6 hours. After reaction, 2.0 g ($3.22\times10^{-3}$ mole) quaternary ammonium salt of hyaluronic acid (Mw=100,000) was dissolved in 18 ml DMSO. 6.2 µl Stannous Octoate and 15.6 mg 1,4-diazabicyclo[2.2.2]octane were dissolved in 2 ml DMSO and added to the quaternary ammonium salt of hyaluronic acid solution. The mPEG prepolymer solution was added to the quaternary ammonium salt of hyaluronic acid solution. The reaction was kept at 60° C. for 16 hours and then quenched with DBA to obtain $HA_{100,000}$-g-30% $PEG_{550}$ copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Example B-20

Synthesis of Hyaluronic Acid Copolymer Grafted with PEG Prepolymer $HA_{16,000}$-g-30% $PEG_{550}$ Copolymer 0.531 g ($9.66\times10^{-4}$ mole) methoxy polyethylene glycols (Mw=550) was dissolved in 1.3 ml DMSO. 1.4 µl Stannous Octoate and 3.6 mg 1,4-diazabicyclo[2.2.2]octane were dissolved in 1 ml DMSO and added to the methoxy polyethylene glycols solution. 0.22 ml 1-isocyanato-4-[(4-isocyanatocyclohexyl)methyl]cyclohexane ($8.69 \times 10^{-4}$ mole) was added to the resulting mixture and the reaction was kept at 60° C. for 6 hours. 2.0 g ($3.22 \times 10^{-3}$ mole) quaternary ammonium salt of hyaluronic acid (Mw=16,000) was dissolved in 6 ml DMSO. 6.2 µl Stannous Octoate and 15.6 mg 1,4-diazabicyclo[2.2.2] octane were dissolved in 2 ml DMSO and added to the quaternary ammonium salt of hyaluronic acid solution. The mPEG prepolymer solution was added to the quaternary ammonium salt of hyaluronic acid solution. The reaction was kept at 60° C. for 16 hours and then quenched with DBA to obtain $HA_{16,000}$-g-30% $PEG_{550}$ copolymer. The reaction mixture was purified in a saturated sodium chloride aqueous solution with a dialysis membrane (MWCO=12,000-14,000). The copolymer was eluted through an ion-exchange resin to replace quaternary ammonium ion to sodium ion, and then freeze-dried.

Anti-enzyme decomposition capability analysis for the hyaluronic acid derivative (1) Preparation of the Sample:

2 mg hyaluronic acid derivative was placed into a 15 ml centrifuge tube. An appropriate amount of hyaluronidase was added into a PBS solution to form a hyaluronidase solution with a concentration of 250 units/ml. 10 ml of the hyaluronidase solution was added into the 15 ml centrifuge tube containing the hyaluronic acid derivative, and then kept at 37° C. (water bath) for 24 hours. The resulting mixture was partitioned on a centrifuge at 4000 G, 25° C. for 20 minutes and then 0.5 ml supernatant was used for uronic acid assay.

(2) Preparation of the Standard Solution:

An appropriate amount of D-glucuronic acid powder was precisely weighted and dissolved in the deionized water to prepare a stock solution for a D-glucuronic acid standard solution. Next, the D-glucuronic acid stock solution was diluted with water to prepare 5 standard solutions with different concentrations (from 0.001% to 0.03%).

(3) Analysis of Enzymatic Degradation:

Equation for calculating the amount of the hyaluronic acid derivative which is not degradation by the enzyme (hyaluronidase):

The hyaluronic acid derivative which is not degradation by the enzyme=$(Cg/Cs) \times Z \times [100/(100-h)] \times (401.3/194.1)$ Cg: Average concentration of D-glucuronic acid in the hyaluronic acid derivative sample solution, represented by mg/g (according to the absorbance value).

Cs: Average concentration of sodium hyaluronate in the hyaluronic acid derivative sample solution, represented by mg/g (according to the concentration of the hyaluronic acid derivative sample solution prepared).

Z: C6H10D7 content percentage in D-glucuronic acid (according to the information from the manufacturer of D-glucuronic acid).

h: Percentage of weight loss on drying (obtained from the experiment of weight loss on drying to the hyaluronic acid derivative powder)

401.3: Relative molecular weight of the di-saccharide region 194.1: Relative molecular weight of glucuronic acid (4) Results of Enzymatic Resistance Analysis:

| Samples | Prepolymer Grafted ratio (%) | hyaluronic acid/hyaluronic acid derivative degradation ratio (%) |
|---|---|---|
| Linear HA1040k | 0 | 74.5 |
| Example A-5 | 7.0 | 39.3 |
| Example A-7 | 16.0 | 41.1 |
| Example A-8 | 17.7 | 42.4 |
| Example B-12 | 100 | 33.1 |

Rheological analysis of hyaluronic acid grafted with a PEG prepolymer (1) Method for Performing Rheological Analysis to the Hyaluronic Acid Derivative Sample Linear hyaluronic acid and HA-g-PEG copolymer were dissolved in distilled water with a concentration of 2 wt %, respectively. Next, the solutions were sonicated at room temperature for 10 minutes and centrifuged at 3000 rpm to remove bubbles therein.

(2) Conditions for Rheological Analysis

Analytical Instrumentation: Anton Paar MCR 301/TA ARES-LS1 rheometer

Conditions for rheological analysis were set as follows:

Testing temperature: 25±0.1° C.;

Viscosity Flow curve shear rate: 0.01-1000 (plate/cup); and

Oscillation Frequency Sweep f(Hz): 0.01-100 (plate/cup).

(3) Results for Rheological Analysis (A)

Figure 14:
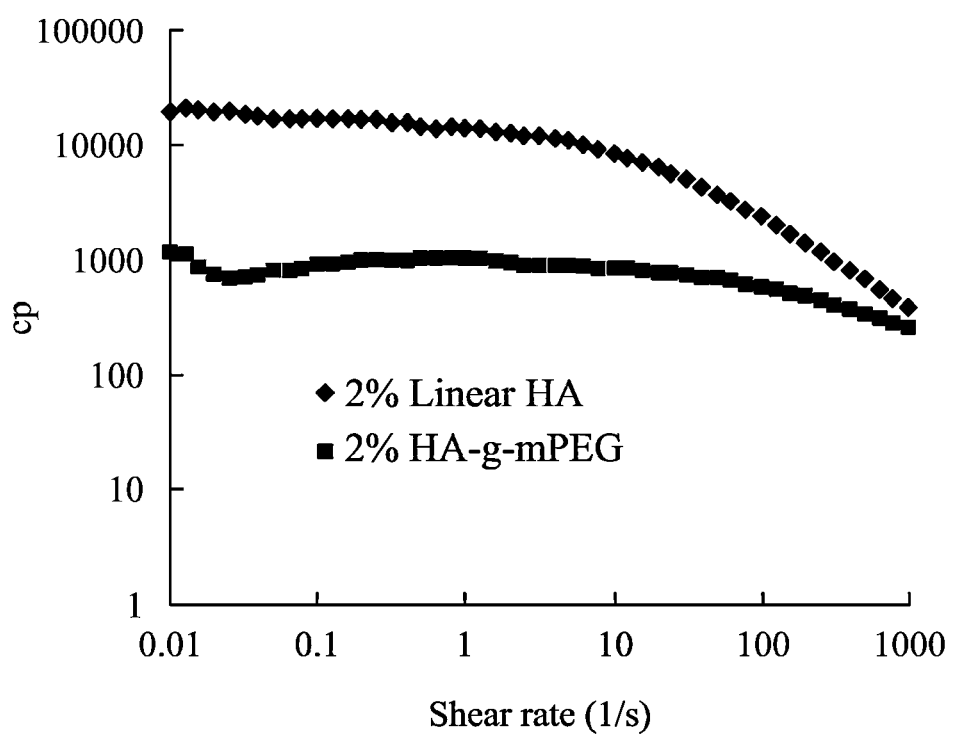
FIG. 14 shows viscosity flow curves of liner HA and HA-g-PEG(A).
Figure 15:
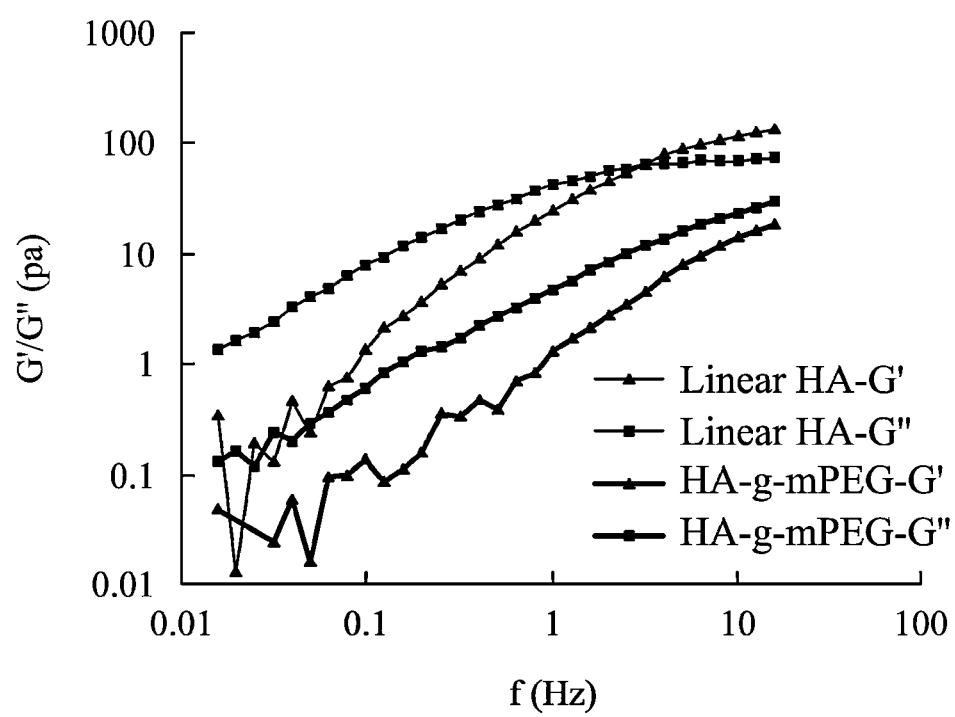
FIG. 15 shows oscillation frequency sweep of liner HA and HA-g-PEG(A).
Figure 16:
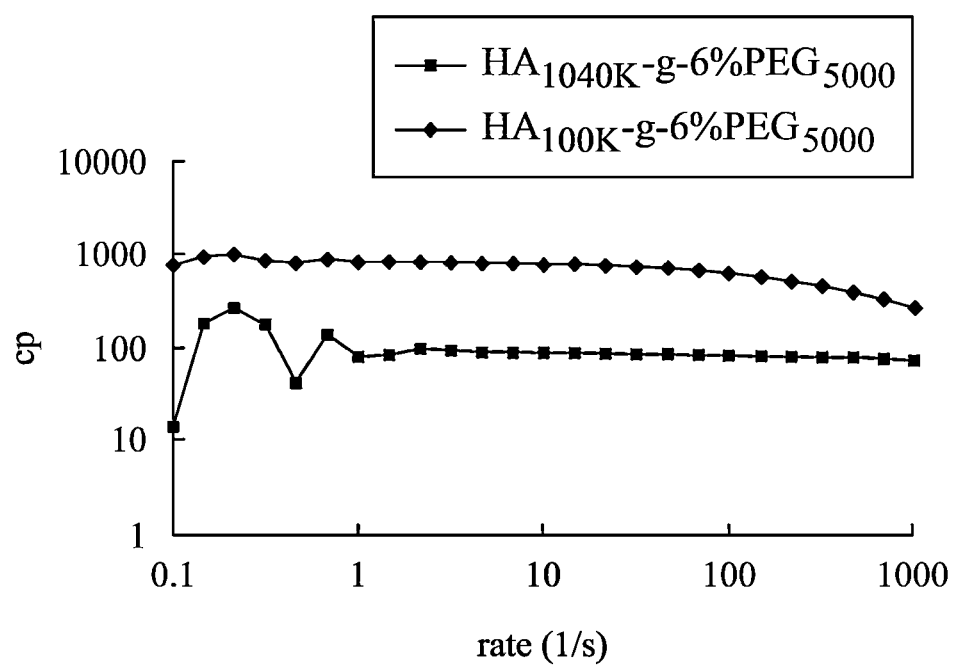
FIG. 16 shows viscosity flow curves of liner HA and HA-g-PEG(B).

FIG. 14 and FIG. 15 show viscosity flow curves and oscillation frequency sweeps for the liner $HA_{1040000}$ and for the $HA_{1040000}$-g-6% $PEG_{5000}$ (Example B-15), respectively. The results show that liner $HA_{1040000}$ present Newtonian fluid characteristics, whereas the $HA_{1040000}$-g-PEG copolymer maintains regular viscosity at different shear rates. However, the viscosity flow curve for $HA_{100000}$-g-6% $PEG_{5000}$ in FIG. 16 shows that the $HA_{100000}$-g-6% $PEG_{5000}$ presents Newtonian fluid characteristics.

(4) Results for Rheological Analysis (B)

Figure 17:
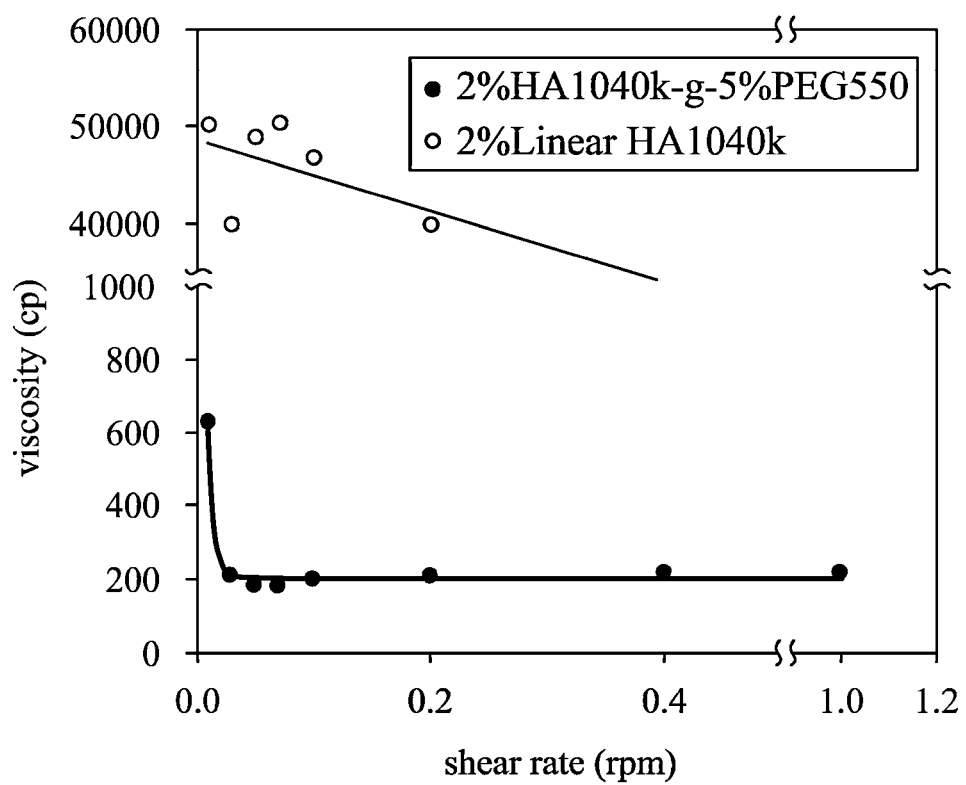
FIG. 17 shows viscosity flow curves of liner $HA_{1040K}$ and $HA_{1040K}$-g-5% $PEG_{550}$.

FIG. 17 shows the viscosity flow curves of linear $HA_{1044000}$ and $HA_{1040000}$-g-6% $PEG_{550}$ copolymer. It represents this copolymer has a decreasing tendency in viscosity in comparison with that of linear $HA_{100000}$. (Analytical Instrumentation: viscometer (Brookfield); testing temperature: 25±0.1; shear rate: 0-1.0 rpm).

In conclusion, the present description modifies a native hyaluronic acid by introducing a short chain moiety or a prepolymer onto the H group via a urethane linkage or degradable ester linkage. The hyaluronic acid derivative of the present description has no cytotoxicity response. Moreover, the hyaluronic acid derivative grafted with a biodegradable hydrophobic prepolymer when dissolved in a hydrophilic medium forms micelles and has a low critical micelle concentration (CMC). Therefore, a pharmaceutically active or bioactive molecule can be entrapped in the hyaluronic acid derivative micelles to form a pharmaceutically active or bioactive composition with a stable controlled released effect.

Combination of hyaluronic acid copolymer grafted with hydrophilic prepolymer and a pharmaceutically active molecule or a bioactive molecule

Example C

Hyaluronic acid and HA-g-PEG copolymer with a concentration of 0.25% were dissolved in D.I. water, a phosphate buffered saline (PBS) and a sucrose solution, respectively, to form three different hyaluronic acid and HA-g-PEG copolymer mixtures, respectively. Then, 0.05% of doxorubicin was added to the three mixtures, respectively and mixed at room temperature for 4 hours to form three different polymer particles. Encapsulation efficiency of drug for the particles and particle sizes are shown in the following table.

| Polymer | Medium | Encapsulation efficiency (EE) of drug (%) | Particle size (nm) |
|---|---|---|---|
| $HA_{100000}$-g-6% $PEG_{5000}$ | D.I. water | 97.3 | 350 ± 50 |
| $HA_{100000}$-g-6% $PEG_{5000}$ | PBS | 46.1 | 450 ± 50 |
| $HA_{16000}$-g-6% $PEG_{5000}$ | sucrose | 94.1 | 200 ± 30 |

Furthermore, a negative charge (—COO⁻) resulting from the —COOH group of the hyaluronic acid derivative in category (A) or category (B) which is soluble in an aqueous solution. A pharmaceutically active or bioactive molecule with a positive charge causes a charge adsorption effect (electrostatic force) which makes the hyaluronic acid derivative in category (A) or category (B) to be a drug carrier. In other words, the pharmaceutically active or bioactive molecule is made to adsorb the hyaluronic acid derivative in category (A) or category (B). When HA-g-hydrophilic prepolymer (e.g. HA-g-PEG) binds to an active molecule (e.g. a drug) which bears a positive charge in an aqueous solution to form a particle, the hydrophilic region of the HA-g-hydrophilic prepolymer (e.g. PEG) is able to prevent agglomeration between particles.

Moreover, for the hyaluronic acid derivative in category (A) or category (B) which is grafted with a long or short chain moiety (such as the hyaluronic acid derivative with a short chain moiety mentioned in the series A examples or the hyaluronic acid grafted with prepolymer mentioned in the series B examples), due to the molecular comformation shielding effect (steric hindrance) resulting from the moiety grafted to the hyaluronic acid, degradation of the hyaluronic acid derivative prepared in this description by hyaluronidase is not easily to accomplished. Namely, the hyaluronic acid derivative prepared in this description is implanted into a human body with a low degradation rate.

The rheological behavior of the hyaluronic acid grafted with the prepolymer mentioned in the series B examples has significant differences in comparison with that of native polymers. When only a few side chains are grafted to the hyaluronic acid, the grafted hyaluronic acid shows a decreasing tendency in viscosity. Therefore, use of the grafted hyaluronic acid with the fluid behavior will be helpful during clinical application (for example, when less force is required for an injection or an injection requires low viscosity characteristics).

While the description has been described by way of example and in terms of the preferred embodiments, it is to be understood that the description is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A biodegradable hyaluronic acid derivative comprising at least one modified hyaluronic acid repeating unit represented by the formula (HA)-[O(C=O)NH-M]$p$, wherein HA is a unit including N-acetyl-D-glucosamine and D-glucuronic acid, M is a modifying moiety containing a C2-16 hydrocarbyl group, and p is an integer of 1 to 4.

2. The biodegradable hyaluronic acid derivative as claimed in claim 1, wherein M is introduced onto the OH group of HA via a urethane linkage or a degradable ester linkage.

3. The biodegradable hyaluronic acid derivative as claimed in claim 1, further comprising a native hyaluronic acid repeating unit including N-acetyl-D-glucosamine and D-glucuronic acid.

4. The biodegradable hyaluronic acid derivative as claimed in claim 1, wherein M is a $C_{2-16}$ alkyl group.

5. The biodegradable hyaluronic acid derivative as claimed in claim 4, wherein M is a $C_{4-12}$ alkyl group.

6. The biodegradable hyaluronic acid derivative as claimed in claim 5, wherein M is butyl, sec-butyl, octyl, or dodecyl.

* * * * *